United States Patent
Ghoroghchian et al.

(10) Patent No.: US 11,213,594 B2
(45) Date of Patent: Jan. 4, 2022

(54) POLY(HISTIDINE)-BASED MICELLES FOR COMPLEXATION AND DELIVERY OF PROTEINS AND NUCLEIC ACIDS

(71) Applicant: Poseida Therapeutics, Inc., San Diego, CA (US)

(72) Inventors: Paiman Peter Ghoroghchian, San Diego, CA (US); Gabriela Romero Uribe, San Diego, CA (US); Eric Ostertag, San Diego, CA (US)

(73) Assignee: POSEIDA THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/097,187

(22) PCT Filed: Apr. 28, 2017

(86) PCT No.: PCT/US2017/030271
§ 371 (c)(1),
(2) Date: Oct. 26, 2018

(87) PCT Pub. No.: WO2017/190091
PCT Pub. Date: Nov. 2, 2017

(65) Prior Publication Data
US 2019/0255191 A1    Aug. 22, 2019

Related U.S. Application Data

(60) Provisional application No. 62/329,892, filed on Apr. 29, 2016, provisional application No. 62/330,775, filed on May 2, 2016, provisional application No. 62/330,784, filed on May 2, 2016.

(51) Int. Cl.
| | | |
|---|---|---|
| A61K 48/00 | (2006.01) |
| A61K 47/69 | (2017.01) |
| A61K 9/107 | (2006.01) |
| A61K 31/7105 | (2006.01) |
| A61K 31/711 | (2006.01) |
| A61K 47/34 | (2017.01) |
| C12N 15/90 | (2006.01) |
| A61K 47/50 | (2017.01) |
| C12N 15/88 | (2006.01) |
| C12N 15/86 | (2006.01) |
| A61K 38/00 | (2006.01) |

(52) U.S. Cl.
CPC .......... *A61K 48/0016* (2013.01); *A61K 9/107* (2013.01); *A61K 31/711* (2013.01); *A61K 31/7105* (2013.01); *A61K 47/34* (2013.01); *A61K 47/50* (2017.08); *A61K 47/6907* (2017.08); *A61K 48/0066* (2013.01); *C12N 15/88* (2013.01); *C12N 15/90* (2013.01); *A61K 38/00* (2013.01); *C12N 15/86* (2013.01)

(58) Field of Classification Search
CPC ................ A61K 48/0016; A61K 47/50; A61K 47/6907; A61K 9/107; A61K 31/7105; A61K 31/711; A61K 47/34; A61K 48/0066; A61K 38/00; C12N 15/86; C12N 15/88; C12N 15/90
See application file for complete search history.

(56) References Cited

U.S. PATENT DOCUMENTS

| | | |
|---|---|---|
| 5,227,170 A | 7/1993 | Sullivan |
| 5,256,422 A | 10/1993 | Albert et al. |
| 5,595,756 A | 1/1997 | Bally et al. |
| 5,612,310 A | 3/1997 | Dewhirst et al. |
| 5,833,974 A | 11/1998 | Teicher |
| 6,133,316 A | 10/2000 | Østensen et al. |
| 6,376,525 B1 | 4/2002 | Kong |
| 6,835,394 B1 | 12/2004 | Discher et al. |
| 7,217,427 B2 | 5/2007 | Discher et al. |
| 7,417,118 B2 | 8/2008 | Kai et al. |
| 7,867,512 B2 | 1/2011 | Discher et al. |
| 7,998,458 B2 | 8/2011 | Sung et al. |
| 8,808,748 B2 | 8/2014 | Ghoroghchian et al. |
| 9,421,247 B2 | 8/2016 | Ghoroghchian et al. |
| 9,533,027 B2 | 1/2017 | Ghoroghchian et al. |
| 10,456,452 B2 | 10/2019 | Ghoroghchian et al. |
| 2003/0114366 A1 | 6/2003 | Martin et al. |

(Continued)

FOREIGN PATENT DOCUMENTS

| | | |
|---|---|---|
| WO | WO 00/02580 A2 | 1/2000 |
| WO | WO 01/080890 A2 | 11/2001 |

(Continued)

OTHER PUBLICATIONS

Meir et al., "Transposon-based Vector Systems for Gene Therapy Clinical Trials: Challenges and Considerations", 2011, Chang Gung Medical Journal 34, 565-578.*

(Continued)

*Primary Examiner* — Scott Long

(74) *Attorney, Agent, or Firm* — Cooley LLP; Ivor Elrifi; Matthew Pavao

(57) ABSTRACT

Disclosed are compositions for delivering gene editing molecules to a cell. Exemplary compositions comprise a micelle assembled from a plurality of triblock copolymers, wherein each triblock copolymer having at least one hydrophobic block, at least one hydrophilic block, and at least one poly(L-histidine) block, wherein: the at least one poly(L-histidine) block complexes with the at least one gene editing molecule; and the at least one poly(L-histidine) block is capable of a pH dependent release of the at least one gene editing molecule.

12 Claims, 15 Drawing Sheets

Specification includes a Sequence Listing.

(56) References Cited

U.S. PATENT DOCUMENTS

| | | |
|---|---|---|
| 2003/0162693 A1 | 8/2003 | Winslow et al. |
| 2003/0180365 A1 | 9/2003 | Barnikol |
| 2004/0265835 A1 | 12/2004 | Lemaster et al. |
| 2005/0019265 A1 | 1/2005 | Hammer et al. |
| 2005/0129747 A1 | 6/2005 | Barnikol et al. |
| 2005/0287145 A1 | 12/2005 | Stewart et al. |
| 2005/0287189 A1 | 12/2005 | Noujaim et al. |
| 2006/0249456 A1 | 11/2006 | Fukutomi et al. |
| 2008/0102128 A1 | 5/2008 | Constancis et al. |
| 2008/0181939 A1 | 7/2008 | Discher et al. |
| 2010/0203149 A1 | 8/2010 | Radosz et al. |
| 2010/0255112 A1 | 10/2010 | Discher et al. |
| 2010/0311168 A1 | 12/2010 | Samuel et al. |
| 2010/0331819 A1 | 12/2010 | Hossainy et al. |
| 2011/0023142 A1 | 1/2011 | Ostertag et al. |
| 2011/0059157 A1 | 3/2011 | Awasthi et al. |
| 2011/0223128 A1 | 9/2011 | Grutzendler et al. |
| 2011/0223217 A1 | 9/2011 | Dixon et al. |
| 2012/0114618 A1 | 5/2012 | Nolta et al. |
| 2013/0177641 A1 | 7/2013 | Ghoroghchian |
| 2013/0202559 A1 | 8/2013 | Skog et al. |
| 2013/0202712 A1 | 8/2013 | Ostertag et al. |
| 2014/0255477 A1 | 9/2014 | Ghoroghchian |
| 2014/0315985 A1 | 10/2014 | May et al. |
| 2014/0363496 A1 | 12/2014 | Ghoroghchian |
| 2015/0232881 A1 | 8/2015 | Glucksmann et al. |
| 2017/0000743 A1 | 1/2017 | Ghoroghchian et al. |
| 2017/0105929 A1 | 4/2017 | Ghoroghchian et al. |
| 2017/0360706 A1 | 12/2017 | Ghoroghchian |
| 2017/0361126 A1 | 12/2017 | Ghoroghchian |
| 2020/0001110 A1 | 1/2020 | Ghoroghchian |
| 2020/0009231 A1 | 1/2020 | Ghoroghchian et al. |
| 2020/0138716 A1 | 5/2020 | Ghoroghchian |
| 2020/0338361 A1 | 10/2020 | Ghoroghchian |

FOREIGN PATENT DOCUMENTS

| | | |
|---|---|---|
| WO | WO 01/89579 A2 | 11/2001 |
| WO | WO 03/059363 A1 | 7/2003 |
| WO | WO 2009/002274 A1 | 12/2008 |
| WO | WO 2009/126705 A2 | 10/2009 |
| WO | WO 2010/118077 A1 | 10/2010 |
| WO | WO 2011/106376 A2 | 9/2011 |
| WO | WO 2011/133635 A2 | 10/2011 |
| WO | WO 2012/094679 A2 | 7/2012 |
| WO | WO 2012/149470 A1 | 11/2012 |
| WO | WO 2014/021408 A1 | 2/2014 |
| WO | WO 2014/093622 A2 | 6/2014 |
| WO | WO 2014/093635 A1 | 6/2014 |
| WO | WO 2015/089462 A1 | 6/2015 |
| WO | WO-2015089462 A1 * | 6/2015 |
| WO | WO 2015/191693 A2 | 12/2015 |
| WO | WO 2016/022805 A1 | 2/2016 |
| WO | WO 2016/090111 A1 | 6/2016 |
| WO | WO 2017/004509 A1 | 1/2017 |

OTHER PUBLICATIONS

Putnam et al., "Polyhistidine-PEG: DNA Nanocomposites for Gene Delivery", 2003, Biomaterials 24, 4425-4433.*

Xie et al., "Seamless gene correction of b-thalassemia mutations in patient-specific iPSCs using CRISPR/Cas9 and piggyBac", 2014, Genome Research 24, 1526-1533.*

Zhang et al., "Poly(L-histidine) Based Triblock Copolymers: pH Induced Reassembly of Copolymer Micelles and Mechanism Underlying Endolysosomal Escape for Intracellular Delivery", 2014, Biomacromolecules 15, 4032-4045.*

Fernando et al., "Sleeping Beauty Transposon-Mediated Nonviral Gene Therapy", 2006, Biodrugs 20, 219-229.*

Nishiyama et al., "Smart polymeric micelles for gene and drug delivery", 2005, Drug Discovery Today: Technologies 2(1), p. 21-26.*

Deng et al., "A biodegradable triblock copolymer poly(ethylene glycol)-bpoly(L-lactide)-b-poly(L-lysine): Synthesis, self-assembly, and RGD peptide modification", 2007, Polymer 48, p. 139-149.*

Hu et al., "pH-responsive and charge shielded cationic micelle of poly(L-histidine)-block-short branched PEI for acidic cancer treatment", 2013, Journal of Controlled Release 172, p. 69-76.*

Cai Yujia, et al., "Targeted genome editing by lentiviral protein transduction of zinc-finger and TAL-effector nucleases.", Elife, vol. 3, pp. 1-19, (Apr. 24, 2014).

Liu Jia, et al., "Efficient delivery of nuclease proteins for genome editing in human stem cells and primary cells", Nature Protocols, vol. 10, No. 11, pp. 1842-1859 (Nov. 2015).

Seow Wei Yang, et al., "A class of cationic triblock amphiphilic of oligopeptides as efficient gene-delivery vectors", Advanced Materials, vol. 21, No. 1, pp. 86-90, (Jan. 5, 2009).

Wiradharma Nikken, et al., "Self-assembled Cationic Peptide Nanoparticles Capable of Inducing Efficient Gene Expression In Vitro," Advanced Functional Materials, vol. 18, No. 6, pp. 943-951 (Mar. 25, 2008).

Zhang Xiaojun et al., "Poly(L-histidine) based triblock copolymers: pH induced reassembly of copolymer micelles and mechanism underlying endolysosomal escape for intracellular delivery," Biomacromolecules, vol. 15, No. 11, pp. 4032-4045, (Nov. 10, 2014).

Hong, Wei et al., "Reversing multidrug resistance by intracellular delivery of Pluronic P85 unimers", Biomaterials, vol. 34, No. 37, pp. 9602-9614 (Dec. 2013).

Lee, et al, "Tumor pH-responsive flower-like micelles of poly(l-lactic acid)-b-poly(ethylene glycol)-b-poly(l-histidine)" Journal of Controlled Release, vol. 123, No. 1, pp. 19-26 (Sep. 26, 2007).

Oh K T et al., "l-Histindine-based pH-sensitive anticancer drug carrier micelle: Reconstituion and brief evaluation of its systemic toxicity" International Journal of Pharmaceutics, vol. 358, No. 1-2, pp. 177-183, (Jun. 24, 2008).

Liu Zhihong, et al., "pH-Sensitive polymeric micelles for programmable drug and gene delivery", Current Pharmaceutical Design, vol. 18, No. 23, pp. 3442-3451, (2012).

Hu Jun et al., "pH-responsive and charge shielded cationic micelle of poly(l-histidine)-block-short branched PEI for acidic cancer treatment", Journal of Controlled Release, vol. 172, No. 1, pp. 69-76, (2013).

Stefan Egli, et al. "Functionalization of Block Copolymer Vesicle Surfaces", Polymers, vol. 3, No. 1, pp. 252-280, (Jan. 11, 2011).

Hong Wei, et al., pH-sensitive micelles for the intracellular co-delivery of curcumin and Pluronic L61 unimers for synergistic reversal effect of multidrug resistance, Scientific Reports, vol. 7, 42465, pp. 1-20, (Feb. 14, 2017).

Adelstein, D.J. et al. (1997) "A Phase III Randomized Trial Comparing Concurrent Chemotherapy and Radiotherapy with Radiotherapy Alone in Resectable Stage III and IV Squamous Cell Head and Neck Cancer: Preliminary Results" *Head and Neck*, 19:567-575.

Ahmed, F. et al. (2006) "Biodegradable Polymersomes Loaded with Both Paclitaxel and Doxorubicin Permeate and Shrink Tumors, Inducing Apoptosis in Proportion to Accumulated Drug" *J Control Release*, 116:150-158.

Ahn, G.O. et al. (2007) "Targeting Tumors with Hypoxia-Activated Cytotoxins" *Frontiers in Bioscience*, 12:3483-3501.

Alarćon, R. et al. (Dec. 1999) "Hypoxia Induces p53 Accumulation through MDM2 Down-Regulation and Inhibition of E6-Mediated Degradation" *Cancer Research*, 59:6046-6054.

Alayash, A.I. (2014) "Blood Substitutes: Why Haven't We Been More Successful?" *Trends Biotechnol*, 32:177-185.

Alberts et al., *Molecular Biology of the Cell*, 3rd ed. New York: Garland Publishing, Inc., 1994; pp. 489-493; pp. 800-801.

American Cancer Society (2010) *Cancer Facts and Figures 2010* [online]. Retrieved from: www.cancer.org/research/cancerfactsfigures/cancerfactsfigures/cancer-facts-and-figures-2010; retreived on Oct. 10, 2011, 62 pages.

Angelova, M.I. et al. (1992) "Preparation of giant vesicles by external AC electric fields. Kinetics and applications" *Prog Coll Polym Sci*, 89:127-131.

(56) References Cited

OTHER PUBLICATIONS

Ansari, A. et al. (1994) "Conformational Relaxation and Ligand-Binding in Myoglobin" *Biochemistry*, 33:5128-5145.
Aquino-Parsons, C. et al. (1999) "Carbogen Inhalation in Cervical Cancer: Assessment of Oxygenation Change" *Gynecologic Oncology*, 74:259-264.
Aranda-Espinoza, H. et al. (Nov. 2001) "Electromechanical Limits of Polymersomes" *Physical Review Letters* 87(20):208301_1-4.
Arifin, D.R. and A.F. Palmer (2003) "Determination of Size Distribution and Encapsulation Efficiency of Liposome-Encapsulated Hemoglobin Blood Substitutes Using Asymmetric Flow Field-Flow Fractionation Coupled with Multi-Angle Static Light Scattering" *Biotechnol Prog*, 19:1798-1811.
Arifin, D.R. and A.F. Palmer (2005) "Polymersome Encapsulated Hemoglobin: A Novel Type of Oxygen Carrier" *Biomacromolecules*, 6:2172-2181.
Ather, M.H. and T.S. Masood (2010) "Current management of advanced and metastatic renal cell carcinoma" *Urology Journal*, 7:1-9.
Bache, M. et al. (2008) "Detection And Specific Targeting of Hypoxic Regions within Solid Tumors: Current Preclinical and Clinical Strategies" *Current Medicinal Chemistry*, 15:322-338.
Bates, F.S. (Feb. 22, 1991) "Polymer-Polymer Phase Behavior" *Science*, 251(4996):898-905.
Benjamini, Y. and Y. Hochberg (1995) "Controlling the false discovery rate: A practical and powerful approach to multiple testing" *Journal of the Royal Statistical Society. Series B (Methodological)*, 57:289-300.
Bermúdez, H. et al. (2002) "Molecular Weight Dependence of Polymersome Membrane Structure, Elasticity, and Stability" *Macromolecules*, 35:8203-8208.
Bermúdez, H. et al. (2004) "Effect of Bilayer Thickness on Membrane Bending Rigidity" *Langmuir*, 20:540-543.
Bernier, J. et al. (2000) "ARCON: Accelerated Radiotherapy with Carbogen and Nicotinamide in Head and Neck Squamous Cell Carcinomas. The Experience of the Cooperative Group of Radiotherapy of the European Organization for Research and Treatment of Cancer (EORTC)", *Radiotherapy and Oncology*, 55:111-119.
Binder, W.H. et al. (2007) "Guiding the Location of Nanoparticles Into Vesicular Structures: A Morphological Study" *Physical Chemistry Chemical Physics*, 9:6435-6441.
Blanazs, A. et al. (2009) "Tailoring Macromolecular Expression at Polymersome Surfaces" *Advanced Functional Materials*, 19:2906-2914.
Bloom, M. et al. (1991) "Physical properties of the fluid lipid-bilayer component of cell membranes: a perspective" *Q Rev Biophys*, 24(3):293-397.
Brahmer, J.R. et al. (2012) " Safety and Activity of Anti-PD-L1 Antibody in Patients with Advanced Cancer" *New England Journal of Medicine*, 366:2455-2465.
Brizel, D.M. et al. (1997) "Tumor Hypoxia Adversely Affects the Prognosis of Carcinoma of the Head and Neck" *International Journal of Radiation Oncology Biology Physics*, 38:285-289.
Brizel, D.M. et al. (1999) "Oxygenation of Head and Neck Cancer: Changes During Radiotherapy and Impact on Treatment Outcome" *Radiotherapy and Oncology*, 53:113-117.
Bromley, E.H.C. et al. (2008) "Peptide and Protein Building Blocks for Synthetic Biology: From Programming Biomolecules to Self-Organized Biomolecular Systems" *ACS Chemical Biology*, 3:38-50.
Brown, J.M. (1999) "The Hypoxic Cell: A Target for Selective Cancer Therapy—Eighteenth Bruce F. Cain Memorial Award Lecture" *Cancer Research*, 59:5863-5870.
Brown, J.M. and L-H. Wang (1998) "Tirapazamine: Laboratory Data Relevant to Clinical Activity" *Anti-Cancer Drug Design*, 13:529-539.
Bunn, H.F. (1995) "The Role of Hemoglobin Based Substitutes in Transfusion Medicine" *Transfus Clin Biol*, 2:433-439.
Bussink, J. et al. (1999) "Clinical Outcome and Tumour Microenvironment Effects of Accelerated Radiotherapy with Carbogen and Nicotinamide" *Acta Oncologica*, 38:875-882.
Cabrales, P. (2013) "Examining and mitigating acellular hemoglobin vasoactivity" *Antioxid Redox Signal*, 18:2329-2341.
Cabrales, P. and J.M. Friedman (2013) "HBOC vasoactivity: interplay between nitric oxide scavenging and capacity to generate bioactive nitric oxide species" *Antioxid Redox Signal*, 18:2284-2297.
Canton, I. et al. (Oct. 2, 2012) "Fully Synthetic Polymer Vesicles for Intracellular Delivery of Antibodies in Live Cells" *The FASEB Journal*, vol. 27, Online Article, www.fasebj.org, doi: 10.1096/fj.12-212183, 11 pages.
Carlson, D.J. et al. (2009) "Towards Temporal Optimization of Radiation Fractionation: The Kinetic Effects of Tumor Hypoxia, DNA Damage Repair, and Tumor Cell Repopulation" *International Journal of Radiation Oncology Biology Physics*, 75:S615-S616; Abstract 1968.
Castillo, R.V. et al. (2010) "Crystallization Kinetics and Morphology of Biodegradable Double Crystalline PLLA-b-PCL Diblock Copolymers" *Macromolecules*, 43:4149-4160.
Chaieb, S. and Rica, S. (Dec. 1998) "Spontaneous curvature-induced pearling instability" *Phys Rev E*, 58(6):7733-7737.
Chance, B. (1991) "Optical Method" *Annual Review of Biophysics and Biophysical Chemistry*, 20:1-28.
Chance, B. et al. (1988) "Time-Resolved Spectroscopy of Hemoglobin and Myoglobin in Resting and Ischemic Muscle" *Analytical Biochemistry*, 174:698-707.
Chang, A. et al. (Jan. 2014) "Chronic Kidney Disease in Patients with Renal Cell Carcinoma" *Advances in Chronic Kidney Disease*, 21:91-95.
Chang, T.M.S. (2006) "Blood substitutes based on nanobiotechnology" *Trends in Biotechnology*, vol. 24, No. 8, p. 372-377.
Chang, T.M.S. (2010) "Blood replacement with nanobiotechnologically engineered hemoglobin and hemoglobin nanocapsules" *Wiley Interdisciplinary Reviews: Nanomedicine and Nanobiotechnology*, 2:418-430.
Chang, Y. et al. (2007) "Sorafenib (BAY 43-9006) inhibits tumor growth and vascularization and induces tumor apoptosis and hypoxia in RCC xenograft models" *Cancer Chemother Pharmacol*, 59:561-574.
Chen, J.Y. et al. (2009) "A Review of Blood Substitutes: Examining the History, Clinical Trial Results, and Ethics of Hemoglobin-Based Oxygen Carriers" *Clinics*, 64:803-813.
Chen, W. et al. (2010) "pH-Sensitive Degradable Polymersomes for Triggered Release of Anticancer Drugs: A Comparative Study with Micelles" *J Control Release*, 142:40-46.
Chin, A.I. et al. (2006) "Surveillance Strategies for Renal Cell Carcinoma Patients Following Nephrectomy" *Reviews in Urology*, 8:1-7.
Cho, D. et al. (2007) "The role of mammalian target of rapamycin inhibitors in the treatment of advanced renal cancer" *Clin Cancer Res*, 13:758s-763s.
Cho, D.C. et al. (2010) "The Efficacy of the Novel Dual PI3-Kinase/mTOR Inhibitor NVP-BEZ235 Compared with Rapamycin in Renal Cell Carcinoma" *Clinical Cancer Research*, 16:3628-3638.
Choueiri, T.K. (Mar. 2008) "Factors associated with outcome in patients with advanced renal cell carcinoma in the era of antiangiogenic agents" *Clin Genitourin Cancer*, 6:15-20.
Choueiri, T.K. (2012) "Efficacy of cabozantinib (XL184) in patients (pts) with metastatic, refractory renal cell carcinoma (RCC)" 2012 ASCO Annual Meeting. *J Clin Oncol*, 30(Suppl):Abstract 4504 [online]. Retrieved from: meeting.library.asco.org/content/95382-114; retrieved on May 4, 2017, 2 pages.
Choueiri, T.K. et al. (2007) "Clinical factors associated with outcome in patients with metastatic clear-cell renal cell carcinoma treated with vascular endothelial growth factor-targeted therapy" *Cancer*, 110:543-550.
Choueiri, T.K. et al. (2007) "Prognostic factors associated with long-term survival in previously untreated metastatic renal cell carcinoma" *Ann Oncol*, 18:249-255.
Christian, D.A. et al. (2009) "Polymersome Carriers: From Self-Assembly To siRNA and Protein Therapeutics" *Eur J Pharm Biopharm*, 71:463-474.

(56) References Cited

OTHER PUBLICATIONS

Christian, D.A. et al. (2010) "Polymer Vesicles with a Red Cell-like Surface Charge: Microvascular Imaging and in vivo Tracking with Near-Infrared Fluorescence" *Macromolecular Rapid Communications*, 31:135-141.

Christian, N.A. et al. (2007) "Tat-Functionalized Near-Infrared Emissive Polymersomes for Dendritic Cell Labeling" *Bioconjugate Chem*, 18:31-40.

Christian, N.A. et al. (2009) "In Vivo Dendritic Cell Tracking Using Fluorescence Lifetime Imaging and Near-Infrared-Emissive Polymersomes" *Mol Imaging Biol*, 11:167-177.

Clifford, S.C. and E.R. Maher (2001) "von Hippel-Lindau disease: clinical and molecular perspectives" *Adv Cancer Res*, 82:85-105.

Conley, K.E. and Jones, C. (1996) "Myoglobin Content and Oxygen Diffusion: Model Analysis of Horse and Steer Muscle" American Journal of Physiology. *Cell Physiology*, 271:C2027-C2036.

Conover, C.D. et al. (Mar. 1999) "The ability of polyethylene glycol conjugated bovine hemoglobin (PEG-Hb) to adequately deliver oxygen in both exchange transfusion and top-loaded rat models" *Artif Cells Blood Substit Immobil Biotechnol*, 27(2):93-107.

Cornelissen, J.J.L.M. et al. (May 29, 1998) "Helical Superstructures from Charged Poly(styrene)-Poly(isocyanodipeptide) Block Copolymers" *Science*, 280:1427-1430.

Courtney, K.D. and T.K. Choueiri (2009) "Optimizing recent advances in metastatic renal cell carcinoma" *Curr Oncol Rep*, 11:218-226.

Courtney, K.D. and T.K. Choueiri (2010) "Updates on novel therapies for metastatic renal cell carcinoma" *Therapeutic Advances in Medical Oncology*, 2:209-219.

Craighead, P.S. et al. (2000) "A Phase I/II Evaluation of Tirapazamine Administered Intravenously Concurrent with Cisplatin and Radiotherapy in Women with Locally Advanced Cervical Cancer" *International Journal of Radiation Oncology Biology Physics*, 48:791-795.

Cristofanilli, M. et al. (Jun. 2002) "Angiogenesis modulation in cancer research: novel clinical approaches" *Nature Reviews Drug Discovery*, 1:415-426.

Csaba et al. "Preparation of Poly(Lactic Acid) (PLA) and Poly(Ethylene Oxide) (PEO) Nanoparticles as Carriers for Gene Delivery" Cold Spring Harb Protocols. vol. 2010, Issue 8, August, pp. 1-4.

De La Fouchardiere, C. et al. (2010) "Phase I Study of Daily Irinotecan As A Radiation Sensitizer for Locally Advanced Pancreatic Cancer" *International Journal of Radiation Oncology Biology Physics*, 77:409-413.

De Wilt, J.H.W. et al. (2000) "Nitric oxide synthase inhibition results in synergistic anti-tumour activity with melphalan and tumour necrosis factor alpha-based isolated limb perfusions" *Br J Cancer*, 83(9):1176-1182.

Deuling, H.J. and W. Helfrich (Nov. 1976) "The Curvature Elasticity of Fluid Membranes: A Catalogue of Vesicle Shapes" *J Phys*, 37:1335-1345.

Dewhirst, M.W. (2009) "Relationships Between Cycling Hypoxia, HIF-1, Angiogenesis and Oxidative Stress" *Radiation Research*, 172:653-665.

Dewhirst, M.W. et al. (1996) "Microvascular Studies on the Origins of Perfusion-Limited Hypoxia" *British Journal of Cancer*, 74:S247-S251.

Dewhirst, M.W. et al. (2007) "Exploring the Role of HIF-1 in Early Angiogenesis and Response to Radiotherapy" *Radiotherapy and Oncology*, 83:249-255.

Dewhirst, M.W. et al. (2008) "Cycling Hypoxia and Free Radicals Regulate Angiogenesis and Radiotherapy Response" *Nature Reviews Cancer*, 8:425-437.

Dewhirst, M.W. et al. (2010) "Utility of Functional Imaging in Prediction or Assessment of Treatment Response and Prognosis Following Thermotherapy" *International Journal of Hyperthermia*, 26:283-293.

Dietz, A. et al. (1999) "Rise of Oxygenation in Cervical Lymph Node Metastasis During the Initial Course of Radiochemotherapy" *Otolaryngology Head and Neck Surgery*, 121:789-796.

Ding, J. and Lieu, G. (1998) "Water-Soluble Hollow Nanospheres as Potential Drug Carriers" *J Phys Chem B*, 102:6107-6113.

Discher, B.M. et al. (May 14, 1999) "Polymersomes: Tough Vesicles Made from Diblock Copolymers" *Science*, 284:1143-1146.

Discher, B.M. et al. (2000) "Polymer Vesicles in Various Media" Curr Opin Colloid Interface Sci, 5:125-131.

Discher, D.E. et al. (2007) "Emerging Applications of Polymersomes in Delivery: From Molecular Dynamics to Shrinkage of Tumors" *Prog Polym Sci*, 32:838-857.

Döbereiner, H.-G. et al. (Apr. 1997) "Mapping vesicle shapes into the phase diagram: A comparison of experiment and theory" *Phys Rev E*, 55:4458-4474.

Dobrowsky, W. (1992) "Mitomycin-C, 5-Fluorouracil and Radiation in Advanced, Locally Recurrent Rectal Cancer" *British Journal of Radiology*, 65:143-147.

Doehn, C. et al. (2009) "Mode-of-Action, Efficacy, and Safety of a Homologous Multi-Epitope Vaccine in a Murine Model for Adjuvant Treatment of Renal Cell Carcinoma" *European Urology*, 56:123-131.

Duncan, T.V. et al. (2008) "Ultrafast Excited-State Dynamics of Nanoscale Near-Infrared Emissive Polymersomes" *J Am Chem Soc*, 130:9773-9784.

Dusenbery, K.E. et al. (1994) "Erythropoietin Increases Hemoglobin During Radiation Therapy for Cervical Cancer" *International Journal of Radiation Oncology Biology Physics*, 29:1079-1084.

Eisbruch, A. et al. (1999) "Bromodeoxyuridine Alternating with Radiation for Advanced Uterine Cervix Cancer: A Phase I and Drug Incorporation Study" Journal of Clinical Oncology, 17:31-40.

English Translation of WO 2014/021408 A1. Obtained from https://patents.google.com/patent/WO2014021408A1/en?oq=nmma+and+paclitaxel on Jul. 9, 2018. Originally published in Japanese on Feb. 6, 2014, 29 printed pages.

Escudier, B. et al. (2014) "Randomized, Controlled, Double-Blind, Cross-Over Trial Assessing Treatment Preference for Pazopanib Versus Sunitinib in Patients with Metastatic Renal Cell Carcinoma: PISCES Study" Journal of Clinical Oncology, 32:1412-1418.

Evans, E. and Needham, D. (1987) "Physical Properties of Surfactant Bilayer Membranes: Thermal Transitions, Elasticity, Rigidity, Cohesion, and Colloidal Interactions" *J Phys Chem*, 91:4219-4228.

Evans, E. and Rawicz, W. (Apr. 23, 1990) "Entropy-Driven Tension and Bending Elasticity in Condensed-Fluid Membranes" *Phys Rev Lett* 64(17):2094-2097.

Evans, S.M. et al. (1997) "Evaluation of the Concept of "Hypoxic Fraction" as a Descriptor of Tumor Oxygenation Status" *Oxygen Transport to Tissue XVIII. Adv Exp Med Biol*, 411:215-225.

Feldman, D.R. et al. (2009) "Phase I Trial of Bevacizumab Plus Escalated Doses of Sunitinib in Patients with Metastatic Renal Cell Carcinoma" *Journal of Clinical Oncology*, 27:1432-1439.

Feldmann, H.J. et al. (1999) "Blood flow and oxygenation status of human tumors. Clinical investigations" *Strahlentherapie Und Onkologie*, 175:1-9.

Fendler, J.H. (Mar. 2, 1984) "Polymerized Surfactant Vesicles: Novel Membrane Mimetic Systems" *Science*, 223(4639):888-894.

Fenton, B.M. et al. (2000) "Enhancement of Tumor Perfusion and Oxygenation by Carbogen and Nicotinamide During Single- and Multifraction Irradiation" *Radiation Research*, 153:75-83.

Figlin, R.A. et al. (May 2008) "Overall survival with sunitinib versus interferon (IFN)-alfa as first-line treatment of metastatic renal cell carcinoma (mRCC)" *Journal of Clinical Oncology*, 26(15 suppl):Abstract 5024 [online]. Retrieved from: http://ascopubs.org/doi/10.1200/jco.2008.26.15_suppl5024; retrieved on May 4, 2017, 2 pages.

Flögel, U. et al. (Apr. 2009) "Myoglobin Tames Tumor Growth and Spread" *Journal of Clinical Investigation*, 119:766-768.

Fogh, S. et al. (2010) "Phase I Trial Using Patupilone (Epothilone B) and Concurrent Radiotherapy for Central Nervous System Malignancies" *International Journal of Radiation Oncology Biology Physics*, 77:1009-1016.

Fontanella, A.N. et al. (2013) "Quantitative Mapping of Hemodynamics in the Lung, Brain, and Dorsal Window Chamber-Grown Tumors Using a Novel, Automated Algorithm" *Microcirculation*, 20:724-735.

(56) References Cited

OTHER PUBLICATIONS

Frauenfelder, H. et al. (Jul. 22, 2003) "Myoglobin: The Hydrogen Atom of Biology and a Paradigm of Complexity" *PNAS*, 100:8615-8617.
Fu, L. et al. (2011) "Generation of a Mouse Model of Von Hippel-Lindau Kidney Disease Leading to Renal Cancers by Expression of a Constitutively Active Mutant of HIF1alpha", *Cancer Research*, 71:6848-6856.
Fyles, A.W. et al. (1998) "Oxygenation Predicts Radiation Response and Survival in Patients with Cervix Cancer" *Radiotherapy and Oncology*, 48:149-156.
Gali-Muhtasib, H. et al. (2004) "Quinoxaline 1,4-Dioxides Are Novel Angiogenesis Inhibitors That Potentiate Antitumor Effects of Ionizing Radiation" *International Journal of Oncology*, 24:1121-1131.
Galluzzo, M. et al. (Apr. 2009) "Prevention of hypoxia by myoglobin expression in human tumor cells promotes differentiation and inhibits metastasis" *J Clin Invest*,119(4):865-875.
Gatzemeier, U. et al. (1998) "Tirapazamine-Cisplatin: The Synergy" *British Journal of Cancer*, 77:15-17.
Ghoroghchian, P.P. et al. (Feb. 2005) "Near-Infrared-Emissive Polymersomes: Self-Assembled Soft Matter for in Vivo Optical Imaging" PNAS, 102:2922-2927.
Ghoroghchian, P.P. et al. (2005) "Broad Spectral Domain Fluorescence Wavelength Modulation of Visible and Near-Infrared Emissive Polymersomes" *J Am Chem Soc*, 127:15388-15390.
Ghoroghchian, P.P. et al. (2006) "Bioresorbable Vesicles Formed through Spontaneous Self-Assembly of Amphiphilic Poly(ethylene oxide)-Block-Polycaprolactone" *Macromolecules*, 39:1673-1675.
Ghoroghchian, P.P. et al. (2006) "Quantitative Membrane Loading of Polymer Vesicles" *Soft Matter*, 2:973-980.
Ghoroghchian, P.P. et al. (2007) "Controlling Bulk Optical Properties of Emissive Polymersomes through Intramembranous Polymer-Fluorophore Interactions" *Chem Mater*, 19:1309-1318.
Ghoroghchian, P.P. et al. (2009) "In Vivo Fluorescence Imaging: A Personal Perspective" *Wire Nanomed Nanobiotechnol*, 1:156-167.
Golshayan, A.R. et al. (Jan. 2009) "Metastatic Sarcomatoid Renal Cell Carcinoma Treated with Vascular Endothelial Growth Factor-Targeted Therapy" Journal of Clinical Oncology, 27:235-241.
Gottschalk, A. et al. (2005) "Influence of the Hemoglobin Solution HBOC-201 on Tissue Oxygenation in the Rat R1H-Tumor" *Artif Cells Blood Substit Biotechnol*, 33:379-389.
Graeber, T.G. et al. (1996) "Hypoxia-Mediated Selection of Cells with Diminished Apoptotic Potential in Solid Tumors" Nature, 379:88-91.
Grepin, R. et al. (2012) "Acceleration of clear cell renal cell carcinoma growth in mice following bevacizumab/Avastin treatment: the role of CXCL cytokines" *Oncogene*, 31:1683-1694.
Grigsby, P.W. et al. (1999) "Irradiation with or without Misonidazole for Patients with Stages IIIB and IVA Carcinoma of the Cervix: Final Results of RTOG 80-05" International Journal of Radiation Oncology Biology Physics, 44:513-517.
Grisanzio, C. et al. (2011) "Orthotopic xenografts of RCC retain histological, immunophenotypic and genetic features of tumours in patients" *Journal of Pathology*, 225:212-221.
Gundersen, S.I. et al. (2008) "Hemoglobin-Based Oxygen Carrier Enhanced Tumor Oxygenation: A Novel Strategy for Cancer Therapy" *Biotechnol Prog*, 24:1353-1364.
Haffty, B.G. et al. (1997) "Chemotherapy as an Adjunct to Radiation in the Treatment of Squamous Cell Carcinoma of the Head and Neck: Results of the Yale Mitomycin Randomized Trials" *J Clin Oncol*, 15:268-276.
Hahn, J.S. et al. (1997) "Stroma-Free Human Hemoglobin A Decreases R3230Ac Rat Mammary Adenocarcinoma Blood Flow and Oxygen Partial Pressure" *Radiation Research*, 147:185-194.
Hai, C. (2012) "Systems Biology of HBOC-Induced Vasoconstriction" *Current Drug Discovery Technologies*, 9:204-211.
Hajduk, D.A. et al. (1998) "Complex Phase Behavior in Aqueous Solutions of Poly(ethylene oxide)-Poly(ethylethylene) Block Copolymers" *J Phys Chem B*, 102:4269-4276.
Hammadi, A. et al. (2008) "Stimulation of iNOS expression and apoptosis resistance in B-cell chronic lymphocytic leukemia (B-CLL) cells through engagement of Toll-like Receptor 7 (TLR-7) and NF-kappaB activation" *Nitric Oxide*, 19:138-145.
Harasym, T.O. et al. (1997) "Intratumor distribution of doxorubicin following i.v. administration of drug encapsulated in egg phosphatidylcholine/cholesterol liposomes" *Cancer Chemother Pharmacol*, 40:309-317.
Hardee, M.E. et al. (2009) "Novel Imaging Provides New Insights into Mechanisms of Oxygen Transport in Tumors" *Current Molecular Medicine*, 9:435-441.
Harrison, L. et al. (2004) "Hypoxia and Anemia: Factors in Decreased Sensitivity to Radiation Therapy and Chemotherapy?" *Oncologist*, 9(Suppl 5):31-40.
Harrison, L.B. et al. (1998) "A Prospective Phase II Trial of Concomitant Chemotherapy and Radiotherapy with Delayed Accelerated Fractionation in Unresectable Tumors of the Head and Neck" *Head Neck*, 20:497-503.
Harrison, L.B. et al. (2002) "Impact of Tumor Hypoxia and Anemia on Radiation Therapy Outcomes" *Oncologist*, 7:492-508.
Hay, M.P. et al. (2004) "DNA-Targeted 1,2,4-Benzotriazine 1,4-Dioxides: Potent Analogues of the Hypoxia-Selective Cytotoxin Tirapazamine" *Journal of Medicinal Chemistry*, 47:475-488.
Hearnden, V. et al. (Jul. 2009) "Diffusion Studies of Nanometer Polymersomes Across Tissue Engineered Human Oral Mucosa" *Pharmaceutical Research*, 26:1718-1728.
Hearnden, V. et al. (2009) "Penetration of Polymersome Drug and Gene Delivery Nanoparticles Into in Vitro Models of Head and Neck Cancer and Tissue Engineered Oral Mucosa" *Oral Abstracts/Oral Oncology*, Supplement 3; p. 66, Abstract O31.
Helcké, G.A. et al. (1968) "Electron Resonance Studies of Haemoglobin Derivatives. III. Line-Width and g-Value Measurements of Acid-Met Myoglobin and of Met Myoglobin Azide Derivatives" *Proceedings of the Royal Society of London Series B-Biological Sciences*, 169:275-288.
Helfand, C. (Jul. 23, 2013) "Top twenty orphan drugs by 2018" *Fierce Pharma.com. Business Insights: Global* [online]. Retrieved from: http://www.fiercepharma.com/special-reports/top-20-orphan-drugs-2018, 2 pages.
Helfrich, W. and Servuss, R.-M. (1984) "Undulations, Steric Interactions and Cohesion of Fluid Membranes" *Il Nuovo Cimento*, 3D(1):137-151.
Henke, M. et al. (1999) "Erythropoietin for Patients Undergoing Radiotherapy: a Pilot Study" *Radiotherapy and Oncology*, 50:185-190.
Henselwood, F. et al. (1998) "Water-Soluble Porous Nanospheres" *Macromolecules*, 31:4213-4217.
Hentze, H.-P. et al. (Jul. 30, 1999) "Lyotropic Mesophases of Poly(ethylene oxide)-b-poly(butadiene) Diblock Copolymers and Their Cross-Linking To Generate Ordered Gels" *Macromolecules*, 32(18):5803-5809.
Herold, S. et al. (2001) "Kinetic and Mechanistic Studies of the NO-Mediated Oxidation of Oxymyoglobin and Oxyhemoglobin" *Biochemistry*, 40:3385-3395.
Hillman, G.G. et al. (2007) "Progression of renal cell carcinoma is inhibited by genistein and radiation in an orthotopic model" *BMC Cancer*, 7:4; doi:10.1186/1471-2407-7-4, 12 pages.
Hillmyer, M.A. and Bates, F.S. (1996) "Synthesis and Characterization of Model Polyalkane-Poly(ethylene oxide) Block Copolymers" *Macromolecules*, 29:6994-7002.
Hillmyer, M.A. et al. (Feb. 16, 1996) "Complex Phase Behavior in Solvent-Free Nonionic Surfactants" *Science*, 271:976-978.
Hochachka, P.W. (Oct. 26, 1999) "The Metabolic Implications of Intracellular Circulation" *PNAS*, 96:12233-12239.
Höckel, M. et al. (1993) "Intratumoral pO2 Predicts Survival in Advanced Cancer of the Uterine Cervix" *Radiotherapy and Oncology*, 26:45-50.
Höckel, M. et al. (1993) "Tumor Oxygenation: A New Predictive Parameter in Locally Advanced Cancer of the Uterine Cervix" *Gynecologic Oncology*, 51:141-149.
Höckel, M. et al. (Oct. 1, 1996) "Association Between Tumor Hypoxia and Malignant Progression in Advanced Cancer of the Uterine Cervix" *Cancer Research* 56:4509-4515.

(56) References Cited

OTHER PUBLICATIONS

Hodi, F.S. et al. (2013) "MPDL3280A (anti-PDL1): Clinical activity, safety and biomarkers of an engineered PD-L1 antibody in patients with locally advanced or metastatic tumors" *European Journal of Cancer*, 49: S184, Abstract 879, 1 page.
Hoogsteen, I.J. et al. (2007) "The Hypoxic Tumour Microenvironment, Patient Selection and Hypoxia-modifying Treatments" *Clinical Oncology*, 19:385-396.
Hoskin, P.J. et al. (1999) "Hypoxic Radiosensitizers in Radical Radiotherapy for Patients with Bladder Carcinoma. Hyperbaric Oxygen, Misonidazole, and Accelerated Radiotherapy, Carbogen, and Nicotinamide" *Cancer*, 86:1322-1328.
Hudes, G. et al. (2007) "Temsirolimus, Interferon Alfa, or Both for Advanced Renal-Cell Carcinoma" *New England Journal of Medicine*, 356:2271-2281.
Hutson, T.E. (2013) "Axitinib versus sorafenib as first-line therapy in patients with metastatic renal cell carcinoma (mRCC)" *Journal of Clinical Oncology*, 31(suppl 6):Abstract LBA348, 1 page.
Hylander, B.L. et al. (2013) "Origin of the vasculature supporting growth of primary patient tumor xenografts" *Journal of Translational Medicine*, 11:110, 14 pages.
Jang, J.S. et al. (2006) "Poly(ethylene glycol)/poly(ε-caprolactone) diblock copolymeric nanoparticles for non-viral gene delivery: The role of charge group and molecular weight in particle formation, cytotoxicity and transfection" *J Cont Rel*, 113:173-182.
Janssen, H.L. et al. (Jul. 2005) "Hypoxia in Head and Neck Cancer: How Much, How Important?" *Head and Neck*, 27:622-638.
Jeffs et al. (Mar. 2005) "A Scalable, Extrusion-Free Method for Efficient Liposomal Encapsulation of Plasmid DNA" *Pharmaceutical Research*, vol. 22, No. 3, p. 362-372.
Kaelin, W.G. Jr. (2004) "The Von Hippel-Lindau Tumor Suppressor Gene and Kidney Cancer" *Clin Cancer Res*, 10(Suppl):6290s-6295s.
Kaelin, W.G. Jr. (Jun. 2005) "ROS: Really Involved in Oxygen Sensing" *Cell Metabolism*, 1:357-358.
Kaelin, W.G. Jr. (Jan. 15, 2007) "The von Hippel-Lindau tumor suppressor protein and clear cell renal carcinoma" *Clin Cancer Res*, 13(2 Suppl):680s-684s.
Kamga, C. et al. (2012) "Myoglobin and mitochondria: A relationship bound by oxygen and nitric oxide" *Nitric Oxide*, 26:251-258.
Kanner, J. et al. (1991) "Nitric-Oxide as an Antioxidant" *Archives of Biochemistry and Biophysics*, 289:130-136.
Karar, J. et al. (2009) "Modulating the Tumor Microenvironment to Increase Radiation Responsiveness" *Cancer Biology & Therapy*, 8:1994-2001.
Katz, D. et al. (2009) "On the Path to Seeking Novel Radiosensitizers" *International Journal of Radiation Oncology Biology Physics*, 73:988-996.
Katz, J.S et al. (2009) "Membrane Stabilization of Biodegradable Polymersomes" *Langmuir*, 25:4429-4434.
Kersey, F.R. et al. (2010) "Stereocomplexed Poly(lactic acid)-Poly(ethylene glycol) Nanoparticles with Dual-Emissive Boron Dyes for Tumor Accumulation" *ACS Nano*, 4:4989-4996.
Keyes, S.R. et al. (Aug. 1985) "Porfiromycin as a Bioreductive Alkylating Agent with Selective Toxicity to Hypoxic EMT6 Tumor Cells in vivo and in vitro" *Cancer Research*, 45:3642-3645.
Keyes, S.R. et al. (Jan. 1985) "Enhancement of Mitomycin C Cytotoxicity to Hypoxic Tumor Cells by Dicoumarol in vivo and in vitro" *Cancer Research*, 45:213-216.
Kim, K.T. et al. (2009) "A Polymersome Nanoreactor with Controllable Permeability Induced by Stimuli-Responsive Block Copolymers" *Advanced Materials*, 21:2787-2791.
Kim, M.S. and Lee, D.S. (2010) "Biodegradable and pH-Sensitive Polymersome with Tuning Permeable Membrane for Drug Delivery Carrier" *Chemical Communications*, 46:4481-4483.
Kim, Y. et al. (2009) "Polymersome Delivery of siRNA and Antisense Oligonucleotides" *J Control Rel*, 134:132-140.
Kirpotin, D. et al. (1996) "Liposomes with detachable polymer coating: destabilization and fusion of dioleoyphosphatidylethanolamine vesicles triggered by cleavage of surface-grafted poly(ethylene glycol)" *FEBS Letters*, 388:115-118.
Kishimura, A. et al. (2007) "Encapsulation of Myoglobin in PEGylated Polyion Complex Vesicles Made from a Pair of Oppositely Charged Block Ionomers: A Physiologically Available Oxygen Carrier" *Angew Chem Int Ed*, 46:6085-6088.
Knocke, T-H. et al. (1999) "Intratumoral pO2-Measurements as Predictive Assay in the Treatment of Carcinoma of the Uterine Cervix" *Radiotherapy and Oncology*, 53:99-104.
Kobayashi, M. et al. (May 2010) "Establishment and Characterization of Transplantable, Luminescence Labeled Rat Renal Cell Carcinoma Cell Lines" *J Urol*, 183:2029-2035.
Kobayashi, M. et al. (2012) "Effect of host immunity on metastatic potential in renal cell carcinoma: the assessment of optimal in vivo models to study metastatic behavior of renal cancer cells" *Tumor Biology*, 33:551-559.
Koch, C.J. et al. (2001) "Pharmacokinetics of EF5 [2-(2-nitro-1-H-imidazol-1-yl)-N-(2,2,3,3,3-pentafluoropropyl) acetamide] in human patients: Implications for hypoxia measurements in vivo by 2-nitrolmidazoles" *Cancer Chemother Pharmacol*, 48:177-187.
Koltover, I. et al. (Jul. 3, 1998) "An Inverted Hexagonal Phase of Cationic Liposome-DNA Complexes Related to DNA Release and Delivery" *Science*, 281:78-81.
Komatsu, T. et al. (1997) "Solid Vesicle Membrane Made of meso-Tetrakis[(bixinylamino)-o-phenyl]porphyrins" *J Am Chem Soc*, 119:11660-11665.
Kondo, A. et al. (Oct. 2001) "Hypoxia-Induced Enrichment and Mutagenesis of Cells That Have Lost DNA Mismatch Repair" *Cancer Research*, 61:7603-7607.
Kondo, K. et al. (2002) "Comprehensive mutational analysis of the VHL gene in sporadic renal cell carcinoma: relationship to clinicopathological parameters" *Genes Chromosomes Cancer*, 34:58-68.
Kondo, K. et al. (2002) "Inhibition of HIF is necessary for tumor suppression by the von Hippel-Lindau protein" *Cancer Cell*, 1:237-246.
Kong, G. et al. (Aug. 15, 2000) "Hyperthermia Enables Tumor-Specific Nanoparticle Delivery: Effect of Particle Size" *Cancer Research*, 60:4440-4445.
Kong, G. et al. (Apr. 1, 2001) "Characterization of the effect of hyperthermia on nanoparticle extravasation from tumor vasculature" *Cancer Research*, 61:3027-3032.
Kooyman, G.L. (1998) "The Physiological Basis of Diving to Depth: Birds and Mammals" *Annual Review of Physiology*, 60:19-32.
Lam, J.S. et al. (2005) "Novel approaches in the therapy of metastatic renal cell carcinoma" *World Journal of Urology*, 23:202-212.
Larkin, J. et al. (2012) "Efficacy of Sequential Treatment with Sunitinib-Everolimus in an Orthotopic Mouse Model of Renal Cell Carcinoma" *Anticancer Research*, 32:2399-2406.
Lavey, R.S. and Dempsey, W.H. (1993) "Erythropoietin Increases Hemoglobin in Cancer-Patients During Radiation Therapy" *International Journal of Radiation Oncology Biology Physics*, 27:1147-1152.
Lee J. et al. (1996) "Direct relationship between radiobiological hypoxia in tumors and monoclonal antibody detection of EF5 cellular adducts" *International Journal of Cancer*, 67:372-378.
Lee, D-J. et al. (1989) "A Phase I/II Study of the Hypoxic Cell Sensitizer Misonidazole as an Adjunct to High Fractional Dose Radiotherapy in Patients with Unresectable Squamous Cell Carcinoma of the Head and Neck: A RTOG Randomized Study (#79-04)" *International Journal of Radiation Oncology Biology Physics*, 16:465-470.
Lee, D-J. et al. (1995) "Results of an rtog phase-III trial (RTOG 85-27) comparing radiotherapy plus etanidazole with radiotherapy alone for locally advanced head and neck carcinomas" *International Journal of Radiation Oncology Biology Physics*, 32:567-576.
Lee, D-J. et al. (1998) "Concurrent Tirapazamine and Radiotherapy for Advanced Head and Neck Carcinomas: A Phase II Study" *International Journal of Radiation Oncology Biology Physics*, 42:811-815.

(56) References Cited

OTHER PUBLICATIONS

Lee, J.C-M. et al. (2001) "Preparation, Stability, and in Vitro Performance of Vesicles Made with Diblock Copolymers" *Biotechnol Bioeng*, 73:135-145.

Lee, J.S. (2011) *Biodegradable Polymersomes for Drug Delivery. Circulation Kinetics and biodistribution, Modulated Drug Delivery and Cellular Uptake*. PhD Thesis, University of Twente, Enschede, The Netherlands; 172 pages.

Lee, J.S. et al. (2012) "Polymersomes for drug delivery: design, formation and characterization" *Journal of Controlled Release*, 161:473-483.

Lee, Y-S. et al. (Feb. 1, 2005) "Coexpression of erythropoietin and erythropoietin receptor in von Hippel-Lindau disease-associated renal cysts and renal cell carcinoma" *Clin Cancer Res*, 11:1059-1064.

Letchford, K. et al. (2007) "A review of the formation and classification of amphiphilic block copolymer nanoparticulate structures: micelles, nanospheres, nanocapsules and polymersomes", *Eur J Pharm Biopharm*, 65:259-269.

Levine, D.H. et al. (2008) "Polymersomes: A New Multi-Functional Tool for Cancer Diagnosis and Therapy" *Methods*, 46:25-32.

Li, S. et al. (2007) "Self-Assembled Poly(Butadiene)-b-Poly(Ethylene Oxide) Polymersomes as Paclitaxel Carriers" *Biotechnol Prog*, 23:278-285.

Liang, X. et al. (2015) "Rapid and highly efficient mammalian cell engineering via Cas9 protein transfection" *J Biotechnol*, 208:44-53.

Liaw, J. et al. (2001) "In Vivo Gene Delivery Into Ocular Tissues by Eye Drops of poly(ethylene oxide)-poly(propylene oxide)-poly(ethylene oxide) (PEO-PPO-PEO) polymeric micelles" *Gene Therapy*, 8:999-1004.

Lim, S.H. et al. (2009) "Effect of Combination of Anticancer Agents and Nitroimidazoles on the Survival of Human Hepatocellular Carcinoma Cells under Hypoxic Conditions" *Journal of the Korean Surgical Society*, 76:337-347. Korean with English Summary on p. 337.

Lin, J.J. et al. (2004) "The Effect of Polymer Chain Length and Surface Density on the Adhesiveness of Functionalized Polymersomes" *Langmuir*, 20:5493-5500.

Lin, J.J. et al. (2006) "Adhesion of Antibody-Functionalized Polymersomes" *Langmuir*, 22:3975-3979.

Lin, Z. et al. (1992) "Cryogenic Electron Microscopy of Rodlike or Wormlike Micelles in Aqueous Solutions of Nonionic Surfactant Hexaethylene Glycol Monohexadecyl Ether" *Langmuir*, 8:2200-2205.

Lipowsky and Sackmann (Eds.) (1995) *Handbook of Biological Physics.vol. 1: Structure and Dynamics of Membranes from Cells to Vesicles*. Amsterdam: Elsevier Science; Chapters 1-10, 513 pages.

Liu, G-Y. et al. (2012) "Biocompatible and biodegradable polymersomes as delivery vehicles in biomedical applications" *Soft Matter*, 8:8811-8821.

Liu, R. et al. (2011) "Anti-tumor drug delivery of pH-sensitive poly(ethylene glycol)-poly(L-histidine-)-poly(L-lactide) nanoparticles" *J Control Rel*, 152:49-56.

Liu, R. et al. (2012) "Effects of pH-sensitive chain length on release of doxorubicin from mPEG-b-PH-b-PLLA nanoparticles" *Intl J Nanomed*, 7:4433-4446.

Liu, R. et al. (2012) "Stabilization of pH-Sensitive mPEG-PH-PLA Nanoparticles by Stereocomplexation Between Enantiomeric Polylactides" *Macromol Rapid Commun*, 33:1061-1066.

Liu, R. et al. (2012) "Synthesis and characterization of poly(ethylene glycol)-b-poly(L-histidine)-b-poly(L-lactide) with pH-sensitivity" *Polymer*, 53:1473-1482.

Liu, S. and O'Brien, D.F. (Aug. 7, 1999) "Cross-Linking Polymerization in Two-Dimensional Assemblies: Effect of the Reactive Group Site" *Macromolecules*, 32:5519-5524.

Lomas, H. et al. (2011) "Polymersome-Loaded Capsules for Controlled Release of DNA" *Small*, 7(14):2109-2119.

Longo, M.L. et al. (Sep. 1997) "Interaction of the Influenza Hemagglutinin Fusion Peptide with Lipid Bilayers: Area Expansion and Permeation" *Biophys J*, 73:1430-1439.

Ma, W.W. and Adjei, A.A. (2009) "Novel agents on the horizon for cancer therapy" *CA Cancer J Clin*, 59:111-137.

Malik, A. et al. (Oct. 1, 2012) "Myoglobin Unfolding in Crowding and Confinement" *J Phys Chem*, 116:12895-12904.

Marzilli, L. et al. (2000) "Peptide sequence information derived by pronase digestion and ammonium sulfate in-source decay matrix-assisted laser desorption/ionization time-of-flight mass spectrometry" *J Am Soc Spectrom*, 11:1000-1008.

Massignani, M. et al. (2009) "Controlling Cellular Uptake by Surface Chemistry, Size, and Surface Topology at the Nanoscale" *Small*, 5:2424-2432.

Mcgee, M.C. et al. (2010) "Improved Intratumoral Oxygenation Through Vascular Normalization Increases Glioma Sensitivity To Ionizing Radiation" *International Journal of Radiation Oncology Biology Physics*, 76:1537-1545.

Melichar, B. et al. (2008) "First-line bevacizumab combined with reduced dose interferon-alpha2a is active in patients with metastatic renal cell carcinoma" *Ann Oncol*, 19:1470-1476.

Meng, F. et al. (Oct. 2012) "Intracellular drug release nanosystems" *Materials Today*, 15(10):436-442.

Meng, F.H. et al. (2005) "Biodegradable polymersomes as a basis for artificial cells: encapsulation, release and targeting" *J Control Release*, 101:187-198.

Meric-Bernstam, F. et al. (May 1, 2009) "Targeting the mTOR signaling network for cancer therapy" *J Clin Oncol*, 27:2278-2287.

Merriam-Webster, Inc. "Electrolyte" in *Merriam-Webster Collegiate® Dictionary. Tenth Edition*. Springfield, Massachusetts, USA: 2002, p. 371.

Mikkelsen, J.G. et al. (Oct. 2003) "Helper-Independent Sleeping Beauty Transposon-Transposase Vectors for Efficient Nonviral Gene Delivery and Persistent Gene Expression in Vivo" *Molecular Therapy*, vol. 8, No. 4, p. 654-665.

Miralbell, R. et al. (1999) "Accelerated Radiotherapy, Carbogen, and Nicotinamide in Glioblastoma Multiforme: Report of European Organization for Research and Treatment of Cancer Trial 22933" *J Clin Oncol*, 17:3143-3149.

Moeller, B.J. and Dewhirst, M.W. (Sep. 2004) "Raising The Bar. How HIF-1 Helps Determine Tumor Radiosensitivity" *Cell Cycle*,3:1107-1110.

Moeller, B.J. et al. (Aug. 2005) "Pleiotropic Effects of HIF-1 Blockade on Tumor Radiosensitivity" *Cancer Cell*, 8:99-110.

Moeller, B.J. et al. (2006) "HIF-1 and tumour radiosensitivity" *British Journal of Cancer*, 95:1-5.

Moeller, B.J. et al. (2007) "Hypoxia and Radiotherapy: Opportunities for Improved Outcomes in Cancer Treatment" *Cancer and Metastasis Reviews*, 26:241-248.

Molina, A.M. et al. (2012) "Phase 1 trial of everolimus plus sunitinib in patients with metastatic renal cell carcinoma" *Cancer*, 118:1868-1876.

Molino, D. et al. (2006) "The history of von Hippel-Lindau disease" *J Nephrol*, 19(Supp):S119-S123.

Moore, E.E. et al. (2009) "Human Polymerized Hemoglobin for the Treatment of Hemorrhagic Shock when Blood Is Unavailable: The USA Multicenter Trial" *Journal of the American College of Surgeons*, 208:1-13.

Motzer, R.J. et al. (2008) "Efficacy of everolimus in advanced renal cell carcinoma: a double-blind, randomised, placebo-controlled phase III trial" *Lancet*, 372:449-456.

Motzer, R.J. et al. (2009) "Overall survival and updated results for sunitinib compared with interferon alfa in patients with metastatic renal cell carcinoma" *J Clin Oncol*, 27:3584-3590.

Motzer, R.J. et al. (2009) "Phase I Trial of Sunitinib Malate plus Interferon-alpha for Patients with Metastatic Renal Cell Carcinoma" *Clinical Genitourinary Cancer*, 7:28-33.

Motzer, R.J. et al. (2012) "Tivozanib versus sorafenib as initial targeted therapy for patients with advanced renal cell carcinoma: Results from a phase III randomized, open-label, multicenter trial" *J Clin Oncol*, 30(Suppl 15):277s, Abstract 4501, 1 page.

Motzer, R.J. et al. (2013) "A phase 3 comparative study of nivolumab (anti-PD-1; BMS-936558; ONO-4538) versus everolimus in patients with advanced or metastatic renal cell carcinoma (mRCC) previously treated with anti-angiogenic therapy" *BJU International*, 112 Suppl 3:10, Abstract 15.

(56) References Cited

OTHER PUBLICATIONS

Motzer, R.J. et al. (2014) "Dovitinib versus sorafenib for third-line targeted treatment of patients with metastatic renal cell carcinoma: an open-label, randomised phase 3 trial" *Lancet Oncology*, 15:286-296.

Mourant, J.R. et al. (Oct. 1993) "Ligand Binding to Heme Proteins: II. Transitions in the Heme Pocket of Myoglobin" *Biophysical Journal*, 65:1496-1507.

Mozzarelli, A. et al. (2010) "Haemoglobin-based oxygen carriers: research and reality towards an alternative to blood transfusions", *Blood Transfus*, 8(Suppl 3):s59-s68.

Mueller, A. et al. (Aug. 22, 1999) "Light-Stimulated Destabilization of PEG-Liposomes" *Polymer Preprints (ACS)*, 40(2):205-206.

Mundt, A.J. et al. (1998) "Race and Clinical Outcome in Patients with Carcinoma of the Uterine Cervix Treated with Radiation Therapy" *Gynecologic Oncology*, 71:151-158.

Musumeci, F. et al. (2012) "Vascular Endothelial Growth Factor (VEGF) Receptors: Drugs and New Inhibitors" *J Med Chem*, 55:10797-10822.

Nagasawa, H. et al. (2006) "Design of Hypoxia-Targeting Drugs as New Cancer Chemotherapeutics" *Biological & Pharmaceutical Bulletin*, 29:2335-2342.

Najafi, F. and Sarbolouki, M.N. (2003) "Biodegradable Micelles/Polymersomes From Fumaric/Sebacic Acids and Poly(Ethylene Glycol)" *Biomaterials*, 24:1175-1182.

Natanson, C. et al. (2008) "Cell-free hemoglobin-based blood substitutes and risk of myocardial infarction and death. A meta-analysis" *JAMA*, 299(19):2304-2312.

Needham, D. and R.S. Nunn (Oct. 1990) "Elastic deformation and failure of lipid bilayer membranes containing cholesterol" *Biophys J*, 58:997-1009.

Needham, D. and Zhelev, D.V. (1996) "The Mechanochemistry of Lipid Vesicles Examined by Micropipet Manipulation Techniques" in *Vesicles*. M. Rosoff (Ed.), New York: Dekker; Chapter 9, pp. 373-444.

Netz, R.R. and M. Schick (Apr. 1996) "Pore formation and rupture in fluid bilayers" *Phys Rev E*, 53(4):3875-3885.

Nienhaus, G.U. et al. (1994) "Ligand Binding to Heme Proteins: The Effect of Light on Ligand-Binding in Myoglobin" *Biochemistry*, 33:13413-13430.

Onaca, O. et al. (2009) "Stimuli-Responseive Polymersomes as Nanocarriers for Drug and Gene Delivery" *Macromolecular Bioscience*, 9:129-139.

O'Neil, C.P. et al. (2009) "A Novel Method for the Encapsulation of Biomolecules into Polymersomes via Direct Hydration" *Langmuir*, 25(16):9025-9029.

Ordway, G.A. and Garry, D.J. (2004) "Myoglobin: An Essential Hemoprotein in Striated Muscle" Journal of Experimental Biology, 207:3441-3446.

Overgaard, J. (1989) "Sensitization of Hypoxic Tumor-Cells—Clinical Experience" *International Journal of Radiation Biology*, 56:801-811.

Overgaard, J. and Horsman, M.R. (1996) "Modification of Hypoxia-Induced Radioresistance in Tumors by the Use of Oxygen and Sensitizers" *Seminars in Radiation Oncology*, 6:10-21.

Overgaard, J. et al. (1989) "Misonidazole Combined with Radiotherapy in the Treatment of Carcinoma of the Uterine Cervix" Int J Radiation Oncology Biol Phys, 16:1069-1072.

Overgaard, J. et al. (1989) "Misonidazole Combined with Split-Course Radiotherapy in the Treatment of Invasive Carcinoma of Larynx and Pharynx: Report From the Dahanca 2 Study" Int J Radiation Oncology Biol Phys, 16:1065-1068.

Overgaard, J. et al. (1998) "A Randomized Double-Blind Phase III Study of Nimorazole as a Hypoxic Radiosensitizer of Primary Radiotherapy in Supraglottic Larynx and Pharynx Carcinoma. Results of the Danish Head and Neck Cancer Study (DAHANCA) Protocol 5-85" *Radiotherapy and Oncology*, 46:135-146.

Özcan, I. et al. (2010) "Pegylation of poly(γ-benzyl-L-glutamate) nanoparticles is efficient for avoiding mononuclear phagocyte system capture in rats" *Intl J Nanomedicine*, 5:1103-1111.

Palaparthy, R. et al. (2000) "Current Aspects in Pharmacology of Modified Hemoglobins" *Adv Drug Deliv Rev*, 40:185-198.

Palmer, A.F. et al. (2009) "Tangential flow filtration of hemoglobin" *Biotechnology Progress*, 25:189-199.

Palmer, G.M. et al. (2009) "Quantitative Diffuse Reflectance and Fluorescence Spectroscopy: Tool to Monitor Tumor Physiology in Vivo" *Journal of Biomedical Optics*, 14(2):024010, 8 pages.

Palmer, G.M. et al. (2010) "Non-Invasive Monitoring of Intra-Tumor Drug Concentration and Therapeutic Response Using Optical Spectroscopy" *J Control Release*, 142:457-464.

Palmer, G.M. et al. (2010) "Optical imaging of tumor hypoxia dynamics" *J Biomed Opt*, 15(6):066021, 7 pages.

Palmer, G.M. et al. (2011) "In vivo optical molecular imaging and analysis in mice using dorsal window chamber models applied to hypoxia, vasculature and fluorescent reporters" *Nat Protoc*, 6:1355-1366.

Pangu, G.D. et al. (2010) "Ultrasonically Induced Release from Nanosized Polymer Vesicles" *Macromol Biosci*, 10:546-554.

Papadopoulou, M.V. et al. (2000) "4-[3-(2-Nitro-1-imidazolyl)propylamino]-7-chloroquinoline Hydrochloride (NLCQ-1), a Novel Bioreductive Agent as Radiosensitizer in Vitro nd in Vivo: Comparison with Tirapazamine" Oncology Research, 12:325-333.

Papadopoulou, M.V. et al. (2000) "4-[3-(2-Nitro-1-imidazolyl)propylamino]-7-chloroquinoline Hydrochloride (NLCQ-1), a Novel Bioreductive Compound as a Hypoxia-Selective Cytotoxin" *Oncology Research*, 12:185-192.

Patel, P.H. et al. (2009) "Phase I Study Combining Treatment with Temsirolimus and Sunitinib Malate in Patients with Advanced Renal Cell Carcinoma" *Clinical Genitourinary Cancer*, 7:24-27.

Patil, S. et al. (Dec. 2012) "Improvement in Overall Survival of Patients with Advanced Renal Cell Carcinoma: Prognostic Factor Trend Analysis from an International Data Set of Clinical Trials" *J Urol*, 188:2095-2100.

Patton, J.N. and Palmer, A.F. (2006) "Physical Properties of Hemoglobin—Poly(acrylamide) Hydrogel-Based Oxygen Carriers: Effect of Reaction pH" *Langmuir*, 22:2212-2221.

Petrov, A.G. and Bivas, I. (1984) "Elastic and Flexoelectric Aspects of Out-of-Plane Fluctuations in biological and Model Membranes" *Prog Surf Sci*, 16:389-511.

Photos, P.J. et al. (2003) "Polymer Vesicles in Vivo: Correlations with PEG Molecular Weight" J Control Release, 90:323-334.

Piras, A. et al. (2008) "Polymeric nanoparticles for hemoglobin-based oxygen carriers" *Biochimica et Biophysica Acta*, 1784:1454-1461.

Privalov, P.L. et al. (1986) "Cold Denaturation of Myoglobin" *J Mol Biol*, 190:487-498.

Qi, W. et al. (2013) "Aqueous self-assembly of poly(ethylene oxide)-block-poly([varepsilon]-caprolactone) (PEO-b-PCL) copolymers: disparate diblock copolymer compositions give rise to nano- and meso-scale bilayered vesicles" *Nanoscale*, 5:10908-10915.

Qiao, Z.-Y. et al. (2013) "Polymersomes from dual responsive block copolymers: Drug encapsulation by heating and acid-triggered release" *Biomacromolecules*, 14:1555-1563.

Rabotyagova, O.S. et al. (2009) "Self-Assembly of Genetically Engineered Spider Silk Block Copolymers" *Biomacromolecules*, 10:229-236.

Rameez, S. et al. (2008) "Biocompatible and Biodegradable Polymersome Encapsulated Hemoglobin: A Potential Oxygen Carrier" *Bioconjugate Chem*, 19:1025-1032.

Rameez, S. et al. (2010) "Large Scale Production of Vesicles by Hollow Fiber Extrusion: A Novel Method for Generating Polymersome Encapsulated Hemoglobin Dispersions" *Langmuir*, 26:5279-5285.

Rameez, S. et al. (2012) "Reactivity of Polymersome Encapsulated Hemoglobin with Physiologically Important Gaseous Ligands: Oxygen, Carbon Monoxide, and Nitric Oxide" *Macromolecules*, 45:2385-2389.

Raval, R.R. et al. (Jul. 2005) "Contrasting properties of hypoxia-inducible factor 1 (H1F-1) and HIF-2 in von Hippel-Lindau-associated renal cell carcinoma" *Mol Cell Biol*, 25:5675-5686.

(56) References Cited

OTHER PUBLICATIONS

Rini, B. et al. (Nov. 20, 2008) "Bevacizumab plus interferon alfa compared with interferon alfa monotherapy in patients with metastatic renal cell carcinoma: CALGB 90206" *J Clin Oncol*, 26:5422-5428.
Rini, B. et al. (Dec. 15, 2012) "AMG 386 in combination with sorafenib in patients with metastatic clear cell carcinoma of the kidney" *Cancer*, 118:6152-6161.
Rischin, D. et al. (Jun. 20, 2010) "Tirapazamine, Cisplatin, and Radiation Versus Cisplatin and Radiation for Advanced Squamous Cell Carcinoma of the Head and Neck (TROG 02.02, HeadSTART): A Phase III Trial of the Trans-Tasman Radiation Oncology Group" *J Clin Oncol*, 28:2989-2995.
Robbins, G.P. et al. (2009) "Photoinitiated Destruction of Composite Porphyrin-Protein Polymersomes", *J Am Chem Soc*, 131:3872-3874.
Robert, C. et al. (2013) "Drug of the year: Programmed Death-1 receptor/Programmed Death-1 Ligand-1 receptor monoclonal antibodies" *European Journal of Cancer*, 49:2968-2971.
Roberts, K.B. et al. (2000) "Interim Results of a Randomized Trial of Mitomycin C as an Adjunct to Radical Radiotherapy in the Treatment of Locally Advanced Squamous-Cell Carcinoma of the Cervix" *Int J Cancer*, 90:206-223.
Robinson, M.F. et al. (1995) "Increased Tumor Oxygenation and Radiation Sensitivity in Two Rat Tumors by A Hemoglobin-Based, Oxygen-Carrying Preparation" *Artif Cells Blood Substit Immobil Biotechnol*, 23:431-438.
Rockwell, S. (1997) "Oxygen Delivery: Implications for the Biology and Therapy of Solid Tumors" *Oncology Research*, 9:383-390.
Rockwell, S. et al. (2009) "Hypoxia and Radiation Therapy: Past History, Ongoing Research, and Future Promise" *Current Molecular Medicine*, 9:442-458.
Rofstad, E.K. et al. (2000) "Hypoxia-Induced Treatment Failure in Advanced Squamous Cell Carcinoma of the Uterine Cervix Is Primarily Due to Hypoxia Induced Radiation Resistance Rather than Hypoxia-Induced Metastasis" British Journal of Cancer, 83:354-359.
Rosenthal, D.I. et al. (1999) "A Phase I Single-Dose Trial of Gadolinium Texaphyrin (Gd-Tex), a Tumor Selective Radiation Sensitizer Detectable by Magnetic Resonance Imaging" *Clinical Cancer Research*, 5:739-745.
Rowinsky, E.K. (Oct. 1999) "Novel Radiation Sensitizers Targeting Tissue Hypoxia" *Oncology*, 13:61-70.
Rudat, V. et al. (2000) "Repeatability and Prognostic Impact of the Pretreatment PO2 Histography in Patients with Advanced Head and Neck Cancer" Radiotherapy and Oncology, 57:31-37.
Sabatini, D.M. (Sep. 2006) "mTOR and cancer: insights into a complex relationship" *Nat Rev Cancer*, 6:729-734.
Sakai, H. et al. (1996) "Functional Evaluation of Hemoglobin- and Lipidheme-vesicles as Red Cell Substitutes" *Polymers for Advanced Technologies*, 7:639-644.
Sakai, H. et al. (2008) "NO and CO Binding Profiles of Hemoglobin Vesicles as Artificial Oxygen Carriers" *Biochimica et Biophysica Acta*, 1784:1441-1447.
Salumbides, B.C. et al. (Dec. 2009) "Pre-clinical models of renal carcinoma and their utility in drug development" *Curr Protoc Pharmacol*, 47:14.13.1-14.13.19.
Sanson, C. et al. (2010) "Temperature Responsive Poly(Trimethylene Carbonate)-Block-Poly(L-Glutamic Acid) Copolymer: Polymersomes Fusion and Fission" *Soft Matter*, 6:1722-1730.
Sartorelli, A.C. et al. (1994) "Mitomycin C: A Prototype Bioreductive Agent" *Oncology Research*, 6:501-508.
Saunders, M. and S. Dische (1996) "Clinical Results of Hypoxic Cell Radiosensitisation from Hyperbaric Oxygen to Accelerated Radiotherapy, Carbogen and Nicotinamide" *British Journal of Cancer*, 74(Suppl. 27):S271-S278.
Schatz, C. et al. (2009) "Polysaccharide-Block-Polypeptide Copolymer Vesicles: Towards Synthetic Viral Capsids" *Angew Chem Int Ed*, 48:2572-2575.

Schmid-Schönbein, H. et al. (1986) "Spectrin, Red Cell Shape and Deformability. I. Membrane Curvature in Genetic Spectrin Deficiency" *Blut*, 52(3):131-147.
Schraml, P. et al. (2002) "VHL mutations and their correlation with tumour cell proliferation, microvessel density, and patient prognosis in clear cell renal cell carcinoma" *J Pathol*, 196:186-193.
Seifert, U. et al. (Jul. 15, 1991) "Shape transformations of vesicles: Phase diagram for spontaneous-curvature and bilayer-coupling models" *Phys Rev A*, 44(2):1182-1202.
Shasha, D. (Jul. 2001) "The Negative Impact of Anemia on Radiotherapy and Chemoradiation Outcomes" *Seminars in Hematology*, 38:8-15.
Shasha, D. et al. (2003) "Once-Weekly Dosing of Epoetin-Alfa Increases Hemoglobin and Improves Quality of Life in Anemic Cancer Patients Receiving Radiation Therapy Either Concomitantly or Sequentially with Chemotherapy" *Cancer*, 98:1072-1079.
Shibamoto, Y. et al. (2001) "In Vivo Evaluation of a Novel Antitumor Prodrug, 1-(2'-Oxopropyl)-5-Fluorouracil (OFU001), Which Releases 5-Fluorouracil Upon Hypoxic Irradiation" *International Journal of Radiation Oncology Biology Physics*, 49:407-413.
Shibayu, M. (2008) "Vascular endothelial growth factor-dependent and -independent regulation of angiogenesis" *BMB Reports*, 41:278-286.
Shih, Y.C. et al. (2011) "Economic burden of renal cell carcinoma in the US. Part II—An updated analysis" *Pharmacoeconomics*, 29:331-341.
Shum, H.C. et al. (2008) "Microfluidic Fabrication of Monodisperse Biocompatible and Biodegradable Polymersomes with Controlled Permeability" *J Am Chem Soc*, 130:9543-9549.
Siemann, D.W. et al. (1998) "Potentiation of Cisplatin Activity By the Bioreductive Agent Tirapazamine" *Radiotherapy and Oncology*, 47:215-220.
Sisson, T.M. et al. (1996) "Cross-Linking Polymerizations in Two-Dimensional Assemblies" *Macromolecules*, 29:8321-8329.
Sivanand, S. et al. (Jun. 6, 2012) "A Validated Tumorgraft Model Reveals Activity of Dovitinib Against Renal Cell Carcinoma" *Science Translational Medicine*, 4:137ra75, including Editor's Summary, 18 pages.
Sivanesaratnam, V. et al. (1989) "Mitomycin C Adjuvant Chemotherapy After Wertheim's Hysterectomy for Stage-IB Cervical Cancer" *Cancer*, 64:798-800.
Smaldone, M.C. et al. (2011) "Adjuvant and Neoadjuvant Therapies in High-Risk Renal Cell Carcinoma" *Hematology/Oncology Clinics of North America*, 25:765-791.
Sonpavde, G. and T.K. Choueiri (2014) "Precision medicine for metastatic renal cell carcinoma" *Urologic Oncology*, 32:5-15.
Sonpavde, G. et al. (2014) "Fibroblast growth factor receptors as therapeutic targets in clear-cell renal cell carcinoma" *Expert Opinion on Investigational Drugs*, 23:305-315.
Sonveaux, P. et al. (2005) "Oxygen Regulation of Tumor Perfusion by S-Nitrosohemoglobin Reveals a Pressor Activity of Nitric Oxide" *Circulation Research*, 96:1119-1126.
Sorg, B.S. et al. (2005) "Hyperspectral Imaging of Hemoglobin Saturation in Tumor Microvasculature and Tumor Hypoxia Development" *Journal of Biomedical Optics*, 10(4):044004, 11 pages.
Sorg, B.S. et al. (Jan./Feb. 2008) "Spectral Imaging Facilitates Visualization and Measurements of Unstable and Abnormal Microvascular Oxygen Transport in Tumors" *Journal of Biomedical Optics*, 13(1):014026, 11 pages.
Stadler, P. et al. (1998) "Changes in Tumor Oxygenation During Combined Treatment with Split-Course Radiotherapy and Chemotherapy in Patients with Head and Neck Cancer" *Radiotherapy and Oncology*, 48:157-164.
Stadler, P. et al. (1999) "Influence of the Hypoxic Subvolume on the Survival of Patients with Head and Neck Cancer" *International Journal of Radiation Oncology Biology Physics*, 44(4):749-754.
Stefely, J. et al. (1988) "Permeability Characteristics of Lipid Bilayers from Lipoic Acid Derived Phosphatidylcholines: Comparison of Monomeric, Cross-Linked and Non-Cross-Linked Polymerized Membranes" *J Am Chem Soc*, 110:7463-7469.
Sternberg, C.N. et al. (2013) "A randomised, double-blind phase III study of pazopanib in patients with advanced and/or metastatic renal

(56) References Cited

OTHER PUBLICATIONS cell carcinoma: Final overall survival results and safety update" *European Journal of Cancer*, 49:1287-1296.

Strube, A. et al. (2010) "Characterization of a new renal cell carcinoma bone metastasis mouse model" *Clin Exp Metastasis*, 27:319-330.

Stüben, G. et al. (1998) "The Effect of Combined Nicotinamide and Carbogen Treatments in Human Tumour Xenografts: Oxygenation and Tumour Control Studies" *Radiotherapy and Oncology*, 48:143-148.

Svetina, S. et al. (1989) "Membrane bending energy and shape determination of phospholipid vesicles and red blood cells" *Eur Biophys J*, 17:101-111.

Szleifer, I. et al. (May 9, 1988) "Curvature Elasticity of Pure and Mixed Surfactant Films" *Phys Rev Lett*, 60(19):1966-1969.

Takeshi, K. et al. (1998) "Definitive radiotherapy combined with high-dose-rate brachytherapy for stage iii carcinoma of the uterine cervix: retrospective analysis of prognostic factors concerning patient characteristics and treatment parameters" *International Journal of Radiation Oncology Biology Physics*, 41:319-327.

Tang, P.A. and Heng, D.Y.C. (2013) "Programmed death 1 pathway inhibition in metastatic renal cell cancer and prostate cancer" *Current Oncology Reports*, 15:98-104.

Tao, Z. et al. (Sep. 2014) "Microparticle, nanoparticle, and stem cell-based oxygen carriers as advanced blood substitutes" *Trends Biotechnol*, 32(9):466-473.

Teicher, B.A. (Apr. 1995) "Physiological Mechamsms of Therapeutic Resistance. Blood Flow and Hypoxia" *Hematology/Oncology Clinics of North America*, 9:475-506.

Teicher, B.A. et al. (1992) "Effect of a Bovine Hemoglobin Preparation on the Response of the FSaIIC Fibrosarcoma to Chemotherapeutic Alkylating Agents" *J Cancer Res Clin Oncol*, 118:123-128.

Teicher, B.A. et al. (1993) "Effect of Hemoglobin Solution on the Response of Intracranial and Subcutaneous Tumors to Antitumor Alkylating-Agents" *Cancer Chemother Pharmacol*, 33:57-62.

Teicher, B.A. et al. (1993) "Oxygenation of Tumors By a Hemoglobin Solution" *J Cancer Res Clin Oncol*,120:85-90.

Teicher, B.A. et al. (1994) "Oxygenation of the Rat-9L Gliosarcoma and the Rat 13672 Mammary Carcinoma with Various Doses of a Hemoglobin Solution" *Artif Cells Blood Substit Immob Biotechnol*, 22:827-833.

Terman, D.S. et al. (Jan. 2013) "Sickle Erythrocytes Target Cytotoxics to Hypoxic Tumor Microvessels and Potentiate a Tumoricidal Response" *PLoS One*, 8:e52543, 11 pages.

Treat, J. et al. (1998) "Tirapazamine with Cisplatin in Patients with Advanced Non-Small-Cell Lung Cancer: A Phase II Study" *Journal of Clinical Oncology*, 16:3524-3527.

Uchegbu, I.F. et al. (1998) "Polymeric Chitosan-based Vesicles for Drug Delivery" *J Pharm Pharmacol*, 50:453-458.

Van Dongen, S.F.M. et al. (2008) "A Block Copolymer for Functionalisation of Polymersome Surfaces", Macromolecular Rapid Communications, 29:321-325.

Víteček, J. et al. (2012) "Arginine-Based Inhibitors of Nitric Oxide Synthase: Therapeutic Potential and Challenges" *Mediators of Inflammation*, 2012:Article ID 318087, 22 pages.

Von Pawel, J. et al. (2000) "Tirapazamine Plus Cisplatin Versus Cisplatin in Advanced Non-Small-Cell Lung Cancer: A Report of the International Catapult I Study Group" *J Clin Oncol*, 18:1351-1359.

Walsh, L. et al. (2006) "Efficacy of ablative high-dose-per-fraction radiation for implanted human renal cell cancer in a nude mouse model" *European Urology*, 50:795-800.

Walter, S. et al. (2012) "Multipeptide immune response to cancer vaccine IMA901 after single-dose cyclophosphamide associates with longer patient survival" *Nature Medicine*, 18:1254-1261.

Wang, et al. (2012) "A novel murine model of human renal cell carcinoma spinal metastasis" *Journal of Clinical Neuroscience*, 19:881-883.

Wang, F. et al. (2009) "Biodegradable Vesicular Nanocarriers Based on Poly(Epsilon-Caprolactone)-Block-Poly(Ethyl Ethylene Phosphate) for Drug Delivery" *Polymer*, 50:5048-5054.

Wang, L. et al. (2012) "Encapsulation of Biomacromolecules within Polymersomes by Electroporation" *Angew Chem Int Ed Engl*, 51:11122-11125.

Warriner, H.E. et al. (Feb. 16, 1996) "Lamellar Biogels: Fluid-Membrane-Based Hydrogels Containing Polymer Lipids" *Science*, 271:969-973.

Wasserman, T.H. et al. (1991) "Clinical-Trials with Etanidazole (SR-2508) by the Radiation Therapy Oncology Group (RTOG)" *Radiotherapy and Oncology*, 20:129-135.

Watanabe, K.I. et al. (2000) "Nitric oxide synthase inhibitor suppresses the ototoxic side effect of cisplatin in guinea pigs" *Anti-cancer Drugs*, vol. 11(5) (Abstract). Obtained from: www.ncbi.nlm.nih.gov/pubmed/10912957 on Jul. 9, 2018. 1 pg.

Wei, Q. et al. (2013) "Aqueous self-assembly of poly(ethylene ozide)-block-poly(ε-caprolactone) (PEO-b-PCL) copolymers: disparate diblock copoymer compositions give rise to nano- and meso-scale bilayered vesicles" *Nanoscale*, 5:10908-10915.

Weitman, S. et al. (1999) "Evidence of Enhanced in Vivo Activity Using Tirapazamine with Paclitaxel and Paraplatin Regimens against the MV-522 Human Lung Cancer Xenograft" *Cancer Chemother Pharmacol*, 43:402-408.

Williams, K.J. et al. (2009) "In Vivo Activation of the Hypoxia-Targeted Cytotoxin AQ4N in Human Tumor Xenografts" *Molecular Cancer Therapeutics*, 8:3266-3275.

Wilson, D. et al. (1998) "Oxygen Distributions within R3230AC Tumors Growing in Dorsal Flap Window Chambers in Rats" *Adv Exp Med Biol*, 454:603-609.

Wittenberg, J.B. and Wittenberg, B.A. (2003) "Myoglobin Function Reassessed" *Journal of Experimental Biology*, 206:2011-2020.

Won, Y-Y. et al. (Feb. 12, 1999) "Giant Wormlike Rubber Micelles" *Science*, 283:960-963.

Wood, C.G. and Filgin, R.A. (2013) "ADAPT: An Ongoing international phase 3 randomized trial of autologous dendritic cell Immunotherapy (AGS 003) plus standard treatment in advanced renal cell carcinoma (RCC)" *BJU International*, 112:11-12, Abstract 18.

Wouters, B.G. et al. (2002) "Hypoxia as a target for combined modality treatments" *European Journal of Cancer*, 38:240-257.

Xu, Feng et al. (2009) "Long-circulation of hemoglobin-loaded polymeric nanoparticles as oxygen carriers with modulated surface charges" *International Journal of Pharmaceuticals*, vol. 377, p. 199-206.

Yildiz, M.E. et al. (2007) "Formation and characterization of polymersomes made by a solvent injection method" *Polymers for Advanced Technologies*, 18:427-432.

Yu, M.H. et al. (2007) "Oxygen carriers and cancer chemo- and radiotherapy sensitization: bench to bedside and back" *Cancer Treatment Reviews*, 33:757-761.

Yu, Y. et al. (1998) "Morphogenic Effect of Solvent on Crew-Cut Aggregates of Amphiphilic Diblock Copolymers" *Macromolecules*, 31:1144-1154.

Yuen, J.S.P. et al. (2011) "Inhibition of angiogenic and non-angiogenic targets by sorafenib in renal cell carcinoma (RCC) in a RCC xenograft model" *British Journal of Cancer*, 104:941-947.

Zhan, H.W. et al. (2010) "Effect of carbogen on tumour oxygenation and 32P-colloid interstitial irradiation response" *Medical Science Monitor*, 16(1):BR11-BR16.

Zhang, G.Q. et al. (Sep. 2009) "A Dual-Emissive-Materials Design Concept Enables Tumour Hypoxia Imaging" *Nature Materials*, 8:747-751.

Zhang, H-H. et al. (2008) "Y-Shaped Poly(ethylene glycol) and Poly(trimethylene carbonate) Amphiphilic Copolymer: Synthesis and for Drug Delivery" *J Polymer Sci: Part A: Polymer Chem*, 46:8131-8140.

Zhang, X.L. et al. (2008) "Key parameters affecting the initial leaky effect of hemoglobin-loaded nanoparticles as blood substitutes", *Journal of Materials Science: Materials in Medicine*, 19:2463-2470.

(56) References Cited

OTHER PUBLICATIONS

Zhao, J. et al. (2007) "Preparation of hemoglobin-loaded nano-sized particles with porous structure as oxygen carriers" *Biomaterials*, 28:1414-1422.

Zupancich, J.A. et al. (2006) "Aqueous Dispersions of Poly(ethylene oxide)-b-poly (γ-methyl-ε-caprolactone) Block Copolymers" *Macromolecules*, 39:4286-4288.

Li, X. et al. (May 30, 2013) "piggyBac transposase tools for genome engineering" *PNAS*, 110(25):E2279-E2287.

Li, L. et al. (Jul. 2015) "Challenges in CRISPR/CAS9 Delivery: Potential Roles of Nonviral Vectors" *Human Gene Therapy*, 26(7):452-462.

Pangburn, T.O. et al. (2012) "Targeted Polymersome Delivery of siRNA Induces Cell Death of Breast Cancer Cells Dependent upon Orai3 Protein Expression" *Langmuir*, 28:12816-12830.

Sui, X. et al. (2015) "Robust formation of biodegradable polymersomes by direct hydration" *Polymer Chemistry*, 6:691-696; first published Nov. 18, 2014.

Tanner, P. et al. (2011) "Polymeric Vesicles: From Drug Carriers to Nanoreactors and Artificial Organelles" *Accts Chem Res*, 44(10):1039-1049.

U.S. Patent Trial and Appeal Board. Decision on Appeal, Apr. 2, 2018. Ex Parte Ghoroghchian et al. Appeal 2017-001943, U.S. Appl. No. 13/508,271; 19 pages and a cover page (20 total sheets).

Yewle, J. et al. (Mar. 2016) "Progressive Saturation Improves the Encapsulation of Functional Proteins in Nanoscale Polymer Vesicles" *Pharmaceutical Research*, 33:573-589.

Yin, H. et al. (Feb. 1, 2016) "Therapeutic Genome Editing by Combined Viral and Non-Viral Delivery of CRISPR System Components in Vivo" *Nature Biotechnology Letters*, 34(3):328-333.

Järver, P. et al. (2008) "Co-transduction of Sleeping Beauty Transposase and Donor Plasmid via a Cell-penetrating Peptide: A simple one step Method" Int J Pept Res Ther, 14:58-63.

Yant, S.R. et al. (2000) "Somatic integration and long-term transgene expression in normal and haemophilic mice using a DNA transposon system" Nat Gen, 25:35-41.

\* cited by examiner

FIGURE 1A

| PLA polumerization time | NP formation method | Mean Size (nm) |
|---|---|---|
| 4 hours | Sonication in PBS | --- |
| 4 hours | TFR in DCM | --- |
| 4 hours | TFR in Acetonitrile | 717 |
| 6 hours | Sonication in PBS | 247 |
| 6 hours | TFR in DCM | 230 |
| 6 hours | TFR in Acetonitrile | 440 |
| 12 hours | Sonication in PBS | 276 |
| 12 hours | TFR in DCM | 958 |
| 12 hours | TFR in Acetonitrile | 335 |

FIGURE 3A

| PHIS polymerization time | NP formation method | Mean Size (nm) |
|---|---|---|
| 48 hours | Sonication in PBS | 789 |
| 48 hours | TFR in DCM | 248 |
| 72 hours | Sonication in PBS | 1680 |
| 72 hours | TFR in DCM | 569 |

FIGURE 4

| pH | Mean Size (nm) | ζ-Potential (mV) |
|---|---|---|
| 4 | 952 ± 158 | ----- |
| 5 | 785 ± 374 | 60.94 |
| 6 | 954 ± 26 | -2.04 |
| 7 | 316 ± 37 | -2.93 |
| 8 | 432 ± 28 | -5.74 |
| 9 | 980 ± 26 | -24.43 |
| 10 | 934 ± 122 | -17.65 |

1. PEO-PLA-PHIS + DNA + mRNA

2. PEO-PLA-PHIS + DNA + mRNA at PH 4.6

3. PEO-PLA-PHIS + DNA + mRNA with SDS

4. DNA Alone

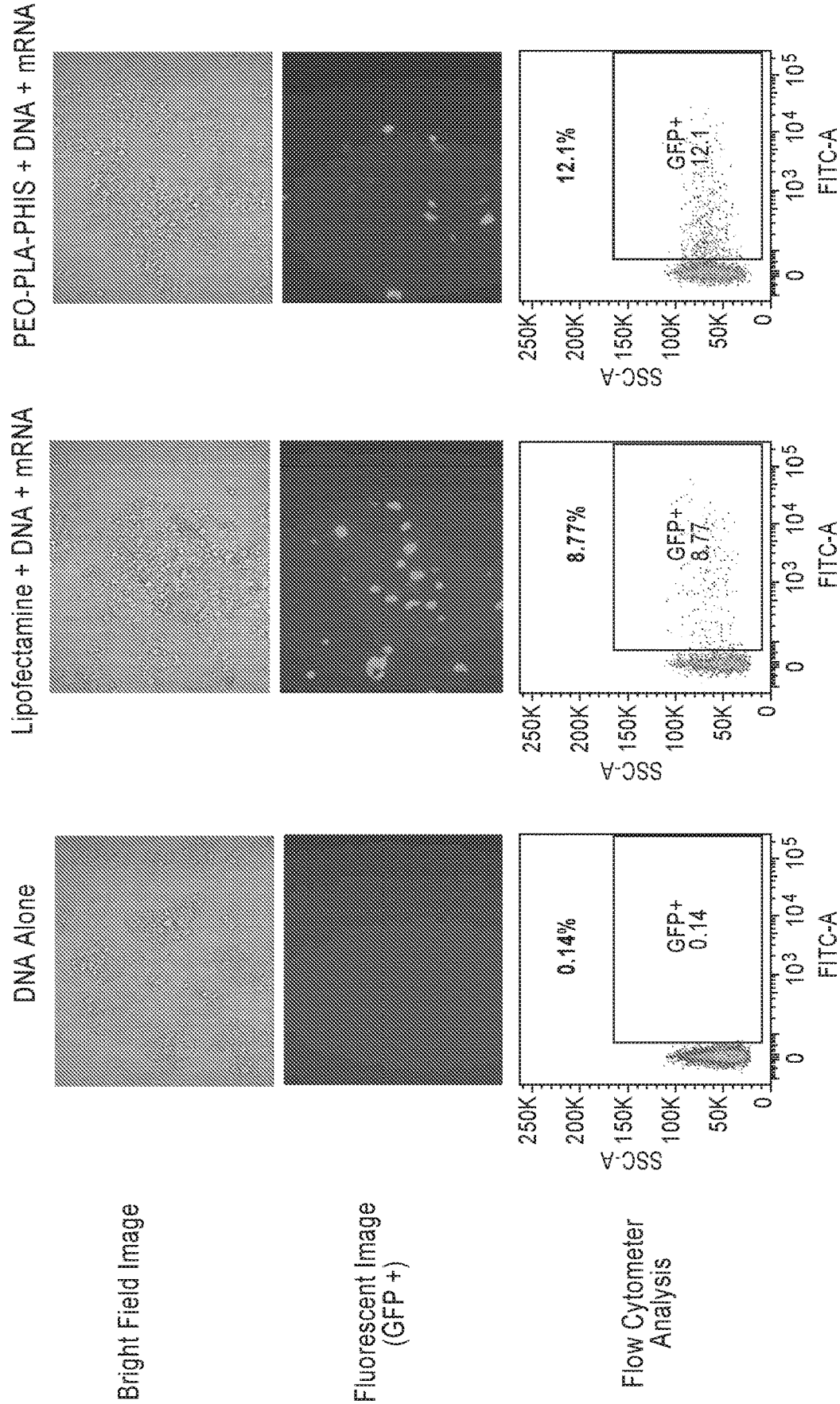

FIGURE 10

| Formulation | GFP | GFP-Transposon | Luc-Transposase |
|---|---|---|---|
| None | 0.2% | 0.4 ± 0.22 % | 0.2 % |
| Lipofectamine | 5.4 ± 0.75 % | 12.88 ± 1.38 % | 15.33 ± 1.94 % |
| PEO-PLA-PHIS | 5.43 ± 0.5 % | 10.48 ± 0.67 % | 14.85 ± 0.79 % |

POLY(HISTIDINE)-BASED MICELLES FOR COMPLEXATION AND DELIVERY OF PROTEINS AND NUCLEIC ACIDS

RELATED APPLICATIONS

This application is a National Stage Application, filed under 35 U.S.C. § 371, of International Application No. PCT/US2017/030271, filed Apr. 28, 2017, which claims priority to U.S. patent application Ser. No. 62/329,892, Apr. 29, 2016, U.S. patent application Ser. No. 62/330,775, May 2, 2016, U.S. patent application Ser. No. 62/330,784, May 2, 2016, the contents of each of which are each herein incorporated by reference in their entirety.

INCORPORATION OF THE SEQUENCE LISTING

The contents of the text file named "POTH-024_N01US SeqListing_ST25.txt", which was created on Mar. 26, 2019 and is 21 KB in size, are hereby incorporated by reference in their entirety.

FIELD OF THE DISCLOSURE

The present invention is directed to compositions and methods for delivery of proteins and nucleic acids, for use in, for example, targeted gene modification.

BACKGROUND

Current mechanisms for delivering proteins and/or nucleic acids to target cells for gene modification including, for example, the use of viral-based gene delivery has limitations including toxicity, aggregation of the protein and/or nucleic acid, payload size limits, and difficulties with large-scale production, including costs and time. Despite a long-felt need in the art, there remains a need for a method of delivering proteins and/or nucleic acids for use in gene modification that overcomes the limitations of the current technology. The disclosure provides a compositions and methods that overcome the limitations of existing technologies.

SUMMARY

The disclosure provides a composition for delivering at least one gene editing molecule to a cell, the composition comprising: a micelle assembled from a plurality of triblock copolymers, wherein each triblock copolymer having at least one hydrophobic block, at least one hydrophilic block, and at least one poly(L-histidine) block, wherein: the at least one poly(L-histidine) block complexes with the at least one gene editing molecule; and the at least one poly(L-histidine) block is capable of a pH dependent release of the at least one gene editing molecule. In certain embodiments of this composition, the at least one gene editing molecule comprises one or more of a protein or a nucleic acid encoding for a protein. In certain embodiments of this composition, the at least one gene editing molecule comprises a protein and the protein is selected from the group comprising a transposase, a nuclease, and an integrase. In certain embodiments of this composition, the at least one gene editing molecule comprises one or more of a protein or a nucleic acid encoding for a protein, wherein the protein is selected from the group comprising a transposase, a nuclease, and an integrase. In certain embodiments of this composition, the nuclease or the protein having nuclease activity is selected from the group comprising: a CRISPR associated protein 9 (Cas9); a type IIS restriction enzyme; a transcription activator-like effector nuclease (TALEN); and a zinc finger nuclease (ZFN).

In certain embodiments of the compositions of the disclosure, the gene editing molecule comprises a DNA-binding domain and a nuclease. In certain embodiments, the DNA-binding domain comprises a guide RNA. In certain embodiments, the DNA-binding domain comprises a DNA-binding domain of a TALEN. In certain embodiments, the DNA-binding domain comprises a DNA-binding domain of a zinc-finger nuclease.

In certain embodiments of the compositions of the disclosure, the CRISPR associated protein 9 (Cas9) is an inactivated Cas9 (dCas9). In certain embodiments, the CRISPR associated protein 9 (Cas9) is truncated or short Cas9. In certain embodiments, the CRISPR associated protein 9 (Cas9) is a short and inactivated Cas9 (dSaCas9). In certain embodiments, the dSaCas9 comprises the amino acid sequence of

```
                                                              (SEQ ID NO: 1)
  1   mkrnyilglA igitsvgygi idyetrdvid agvrlfkean vennegrrsk rgarrlkrrr 61   rhriqrvkkl lfdynlltdh selsginpye arvkglsqkl seeefsaall hlakrrgvhn 121   vneveedtgn elstkeqisr nskaleekyv aelqlerlkk dgevrgsinr fktsdyvkea 181   kqllkvqkay hqldqsfidt yidlletrrt yyegpgegsp fgwkdikewy emlmghctyf 241   peelrsvkya ynadlynaln dlnnlvitrd enekleyyek fqiienvfkq kkkptlkqia 301   keilvneedi kgyrvtstgk peftnlkvyh dikditarke iienaelldq iakiltiyqs 361   sediqeeltn lnseltqeei eqisnlkgyt gthnlslkai nlildelwht ndnqiaifnr 421   lklvpkkvdl sqqkeipttl vddfilspvv krsfiqsikv inaiikkygl pndiiielar 481   eknskdaqkm inemqkrnrq tnerieeiir ttgkenakyl iekiklhdmq egkclyslea 541   ipledllnnp fnyevdhiip rsvsfdnsfn nkvlvkqeeA skkgnrtpfq ylsssdskis 601   yetfkkhiln lakgkgrisk tkkeylleer dinrfsvqkd finrnlvdtr yatrglmnll 661   rsyfrvnnld vkvksinggf tsflrrkwkf kkernkgykh haedaliian adfifkewkk 721   ldkakkvmen qmfeekqaes mpeieteqey keifitphqi khikdfkdyk yshrvdkkpn
```

```
 781    relindtlys  trkddkgntl  ivnnlnglyd  kdndklkkli  nkspekllmy  hhdpqtyqkl 841    klimeqygde  knplykyyee  tgnyltkysk  kdngpvikki  kyygnklnah  lditddypns 901    rnkvvklslk  pyrfdvyldn  gvykfvtvkn  ldvikkenyy  evnskcyeea  kklkkisnqa 961    efiasfynnd  likingelyr  vigvnndlln  rievnmidit  yreylenmnd  krppriikti 1021    asktqsikky  stdilgnlye  vkskkhpqii  kkg.
```

In certain embodiments of the compositions of the disclosure, the type IIS restriction enzyme comprises one or more of AciI, MnlI, AlwI, BbvI, BccI, BceAI, BsmAI, BsmFI, BspCNI, BsrI, BtsCI, HgaI, HphI, HpyAV, MboII, MylI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. In certain embodiments, the type IIS restriction enzyme comprises Clo051.

In certain embodiments of the compositions of the disclosure, the DNA binding domain or the nuclease comprises a sequence isolated or derived from a Ralstonia TALEN or from a Xanthomonas TALEN. In certain embodiments, the DNA binding domain or the nuclease comprises a recombinant TALEN sequence derived from a Ralstonia TALEN, a Xanthomonas TALEN or a combination thereof.

In certain embodiments of the compositions of the disclosure, the at least one gene editing molecule comprises one or more transposable element(s). In certain embodiments, the one or more transposable element(s) comprise a circular DNA. In certain embodiments, the one or more transposable element(s) comprise a plasmid vector or a minicircle DNA vector.

In certain embodiments of the compositions of the disclosure, the at least one gene editing molecule comprises one or more transposable element(s). In certain embodiments, the one or more transposable element(s) comprise a linear DNA. The linear recombinant and non-naturally occurring DNA sequence encoding a transposon may be produced in vitro. Linear recombinant and non-naturally occurring DNA sequences of the disclosure may be a product of a restriction digest of a circular DNA. In certain embodiments, the circular DNA is a plasmid vector or a minicircle DNA vector. Linear recombinant and non-naturally occurring DNA sequences of the disclosure may be a product of a polymerase chain reaction (PCR). Linear recombinant and non-naturally occurring DNA sequences of the disclosure may be a double-stranded Doggybone™ DNA sequence. Doggybone™ DNA sequences of the disclosure may be produced by an enzymatic process that solely encodes an antigen expression cassette, comprising antigen, promoter, poly-A tail and telomeric ends.

In certain embodiments of the compositions of the disclosure, the at least one gene editing molecule comprises one or more transposable element(s). In certain embodiments, the one or more transposable element(s) comprise a piggyBac transposon, a Sleeping Beauty transposon or a LINE-1 (L1) transposon.

In certain embodiments of the compositions of the disclosure, including those embodiments wherein the at least one gene editing molecule comprises one or more transposable element(s), the at least one gene editing molecule comprises further comprises one or more transposase(s). In certain embodiments, including those embodiments wherein the transposon is a piggyBac transposon, the transposase is a Super piggyBac (sPBo) transposase. In certain embodiments, the Super piggyBac (PB) transposase enzyme may comprise or consist of an amino acid sequence at least 75% identical to:

(SEQ ID NO: 2)
MGSSLDDEHILSALLQSDDELVGEDSDSEVSDHVSEDDVQSDTEEAFIDE

VHEVQPTSSGSEILDEQNVIEQPGSSLASNRILTLPQRTIRGKNKHCWST

SKSTRRSRVSALNIVRSQRGPTRMCRNIYDPLLCFKLFFTDEIISEIVKW

TNAEISLKRRESMTSATFRDTNEDEIYAFFGILVMTAVRKDNHMSTDDLF

DRSLSMVYVSVMSRDREDFLIRCLRMDDKSIRPTLRENDVFTPVRKIWDL

FIHQCIQNYTPGAHLTIDEQLLGFRGRCPFRVYIPNKPSKYGIKILMMCD

SGTKYMINGMPYLGRGTQTNGVPLGEYYVKELSKPVHGSCRNITCDNWFT

SIPLAKNLLQEPYKLTIVGTVRSNKREIPEVLKNSRSRPVGTSMFCFDGP

LTLVSYKPKPAKMVYLLSSCDEDASINESTGKPQMVMYYNQTKGGVDTLD

QMCSVMTCSRKTNRWPMALLYGMINIACINSFIIYSHNVSSKGEKVQSRK

KFMRNLYMSLTSSFMRKRLEAPTLKRYLRDNISNILPKEVPGTSDDSTEE

PVMKKRTYCTYCPSKIRRKANASCKKCKKVICREHNIDMCQSCF.

In certain embodiments of the compositions of the disclosure, including those embodiments wherein the at least one gene editing molecule comprises one or more transposable element(s), the at least one gene editing molecule comprises further comprises one or more transposase(s). In certain embodiments, including those embodiments wherein the transposon is a Sleeping Beauty transposon, the transposase is a Sleeping Beauty 100X (SB100X) transposase. In certain embodiments, the Sleeping Beauty transposase enzyme comprises an amino acid sequence at least 75% identical to:

(SEQ ID NO: 3)
MGKSKEISQDLRKKIVDLHKSGSSLGAISKRLKVPRSSVQTIVRKYKHHG

TTQPSYRSGRRRYLSPRDERTLVRKVQINPRTTAKDLVKMLEETGTKVSI

STVKRVLYRHNLKGRSARKKPLLQNRHKKARLRFATAHGDKDRTFWRNVL

WSDETKIELFGHNDHRYVWRKKGEACKPKNTIPTVKHGGGSIMLWGCFAA

GGTGALHKIDGIMRKENYVDILKQHLKTSVRKLKLGRKWVFQMDNDPKHT

SKVVAKWLKDNKVKVLEWPSQSPDLNPIENLWAELKKRVRARRPTNLTQL

HQLCQEEWAKIHPTYCGKLVEGYPKRLTQVKQFKGNATKY.

In certain embodiments, including those wherein the Sleeping Beauty transposase is a hyperactive Sleeping Beauty SB100X transposase, the Sleeping Beauty transposase enzyme comprises an amino acid sequence at least 75% identical to:

(SEQ ID NO: 4)
MGKSKEISQDLRKRIVDLHKSGSSLGAISKRLAVPRSSVQTIVRKYKHHGT
TQPSYRSGRRRYLSPRDERTLVRKVQINPRTTAKDLVKMLEETGTKVSIST
VKRVLYRHNLKGHSARKKPLLQNRHKKARLRFATAHGDKDRTFWRNVLWSD
ETKIELFGHNDHRYVWRKKGEACKPKNTIPTVKHGGGSIMLWGCFAAGGTG
ALHKIDGIMDAVQYVDILKQHLKTSVRKLKLGRKWVFQHDNDPKHTSKVVA
KWLKDNKVKVLEWPSQSPDLNPIENLWAELKKRVRARRPTNLTQLHQLCQE
EWAKIHPNYCGKLVEGYPKRLTQVKQFKGNATKY.

The disclosure provides a pharmaceutical composition for delivering at least one gene editing molecule to a cell, the composition comprising: a micelle assembled from a plurality of triblock copolymers, wherein each triblock copolymer having at least one hydrophobic block, at least one hydrophilic block, and at least one poly (L-histidine) block, wherein: the at least one poly (L-histidine) block complexes with the at least one gene editing molecule; and the at least one poly (L-histidine) block is capable of a pH dependent release of the at least one gene editing molecule.

The disclosure provides a kit, comprising: a pharmaceutical composition for delivering at least one gene editing molecule to a cell, the composition comprising: a micelle assembled from a plurality of triblock copolymers, wherein each triblock copolymer having at least one hydrophobic block, at least one hydrophilic block, and at least one poly (L-histidine) block, wherein: the at least one poly (L-histidine) block complexes with the at least one gene editing molecule; and the at least one poly (L-histidine) block is capable of a pH dependent release of the at least one gene editing molecule; and an implement for administering the pharmaceutical composition. In certain embodiments, the pharmaceutical composition is administered systemically or locally. In certain embodiments, the pharmaceutical composition is administered intravenously, via inhalation, topically, per rectum, per the vagina, transdermally, subcutaneously, intraperitoneally, intrathecally, intramuscularly or orally.

The disclosure provides a kit, comprising: a pharmaceutical composition for delivering at least one gene editing molecule to a cell, the composition comprising: a micelle assembled from a plurality of triblock copolymers, wherein each triblock copolymer having at least one hydrophobic block, at least one hydrophilic block, and at least one poly (L-histidine) block, wherein: the at least one poly (L-histidine) block complexes with the at least one gene editing molecule; and the at least one poly (L-histidine) block is capable of a pH dependent release of the at least one gene editing molecule; and an implement for administering the pharmaceutical composition intravenously, via inhalation, topically, per rectum, per the vagina, transdermally, subcutaneously, intraperitoneally, intrathecally, intramuscularly or orally.

In certain embodiments of the compositions of the disclosure, including pharmaceutical compositions of the disclosure, the compositions comprise a micelle structure comprising a triblock copolymer capable of complexing with at least one protein or nucleic acid, wherein the triblock copolymer comprises a hydrophilic block a hydrophobic block, and a poly(L-histidine) block. In certain embodiments of the triblock copolymer, the hydrophilic block comprises poly(ethylene oxide) (PEO). In certain embodiments of the triblock copolymer, the hydrophilic block comprises at least one aliphatic polyester. In certain embodiments of the triblock copolymer, the hydrophilic block comprises a poly (lactic acid), a poly(glycolic acid) (PGA), a poly(lactic-co-glycolic acid) (PLGA), a poly(ε-caprolactone) (PCL), a poly(3-hydroxybutyrate) (PHB) or any combination thereof. In certain embodiments of the triblock copolymer, the hydrophilic block comprises a poly(lactic acid) having an average length of 25 units.

In certain embodiments of the compositions of the disclosure, including pharmaceutical compositions of the disclosure, the compositions comprise a micelle structure comprising a triblock copolymer capable of complexing with at least one protein or nucleic acid, wherein the triblock copolymer comprises a hydrophilic block a hydrophobic block, and a poly(L-histidine) block. In certain embodiments of the triblock copolymer, the hydrophobic block comprises a poly(ester), a poly(anhydride), a poly(peptide), an artificial poly(nucleic acid) or any combination thereof.

In certain embodiments of the compositions of the disclosure, including pharmaceutical compositions of the disclosure, the compositions comprise a micelle structure comprising a triblock copolymer capable of complexing with at least one protein or nucleic acid, wherein the triblock copolymer comprises a hydrophilic block a hydrophobic block, and a poly(L-histidine) block. In certain embodiments of the triblock copolymer, the poly(L-histidine) block enables pH-dependent release of the at least one protein or nucleic acid. Exemplary poly(L-histidine) copolymers include, but are not limited to, non-degradable and degradable diblocks. Exemplary degradable poly(L-histidine) copolymers include, but are not limited to, PEO(5000)-b-PCL(16300) ("P2350-EOCL"); PEO(2000)-b-PMCL (11900) ("OCL"); PEO(2000)-b-PMCL(8300) ("OMCL"); PEO(1100)-b-PTMC(5100) ("OTMC"); and PEO(2000)-b-PTMC/PCL(11200) ("OTCL").

In certain embodiments of the compositions of the disclosure, including pharmaceutical compositions of the disclosure, the compositions comprise a micelle structure comprising a copolymer comprising PEO-b-PLA-b PHIS. In certain embodiments, the PEO block may comprise at least 1 monomer, 5 monomers, 10 monomers, 100 monomers, 500 monomers, 1000 monomers, 2500 monomers, 5000 monomers, 10000 monomers, 15000 monomers or any number of monomers in between. In certain embodiments, the PLA block may comprise at least 1 monomer, 5 monomers, 10 monomers, 100 monomers, 500 monomers, 1000 monomers, 2500 monomers, 5000 monomers, 10000 monomers, 15000 monomers or any number of monomers in between. In certain embodiments, the PHIS block may comprise at least 1 monomer, 5 monomers, 10 monomers, 100 monomers, 500 monomers, 1000 monomers, 2500 monomers, 5000 monomers, 10000 monomers, 15000 monomers or any number of monomers in between.

In certain embodiments of the compositions of the disclosure, including pharmaceutical compositions of the disclosure, the compositions comprise a micelle structure comprising a copolymer comprising PEO-b-PLA-b PHIS. In certain embodiments, the molar ratio of polymer to cargo is 20:1, 15:1, 10:1, 5:1, or 2:1. In certain embodiments, the cargo is at least one gene editing molecule of the disclosure.

BRIEF DESCRIPTION OF THE DRAWINGS

FIG. 1A is a table depicting PLA polymerization times, micelle formation techniques, and mean diameter sizes of nanoparticles in the diblock copolymer micelle model of Example 1. As shown, using the particular test combination of PLA polymerization for 6 hours (25 PLA units) and sonication of the copolymers in phosphate-buffered saline (PBS), the mean diameter of the resulting micelles was 247 nm.

FIG. 3A is a table depicting PHIS polymerization times, micelle formation techniques, and mean diameter sizes of the resulting nanoparticles of the diblock copolymer micelle model of Example 1. Using the particular combination of PHIS polymerization for 48 hours and thin film rehydration (TFR) of the block copolymers in dichloromethane (DCM) of the copolymers in PBS, the mean diameter of the resulting micelles was 248 nm.

FIG. 4 is a table depicting the variation in properties of the PEO-b-PLA-b-PHIS micelles in different pHs was tested. As shown, the micelles were the smallest at a pH of around 7, with a mean diameter size of around 316 nm. When the pH was substantially raised or lowered, the mean diameter size increases. At the lower pH, such increase is likely due to the micelle swelling based on poly(histidine) chains gaining positive charges and growing.

FIG. 7 is a series of photographs and FACS plots showing the transfection efficiency results from Example 1. HepG2 cells were seeded overnight in 24-well plates at 50,000 cells/well. Cell were exposed to different formulations in Opti-MEM Media (DNA alone, Lipofectamine+DNA+mRNA and PEO-PLA-PHIS+DNA+mRNA) at a final concentration of 500 ng of DNA per well. At 48 hours post-incubation, cells were analyzed for GFP expression by microscopy and flow cytometry to determine the transfection efficiency for each condition.

FIG. 10 is a graph depicting piggyBac delivery via polymeric micelles. Evaluation of transfection efficiency in HepG2 cells. HepG2 cells were incubated with plasmid or micelle formulation containing plasmid for 3 days. Flow cytometer was to detect transfected cells.

DETAILED DESCRIPTION

Figure 1B:
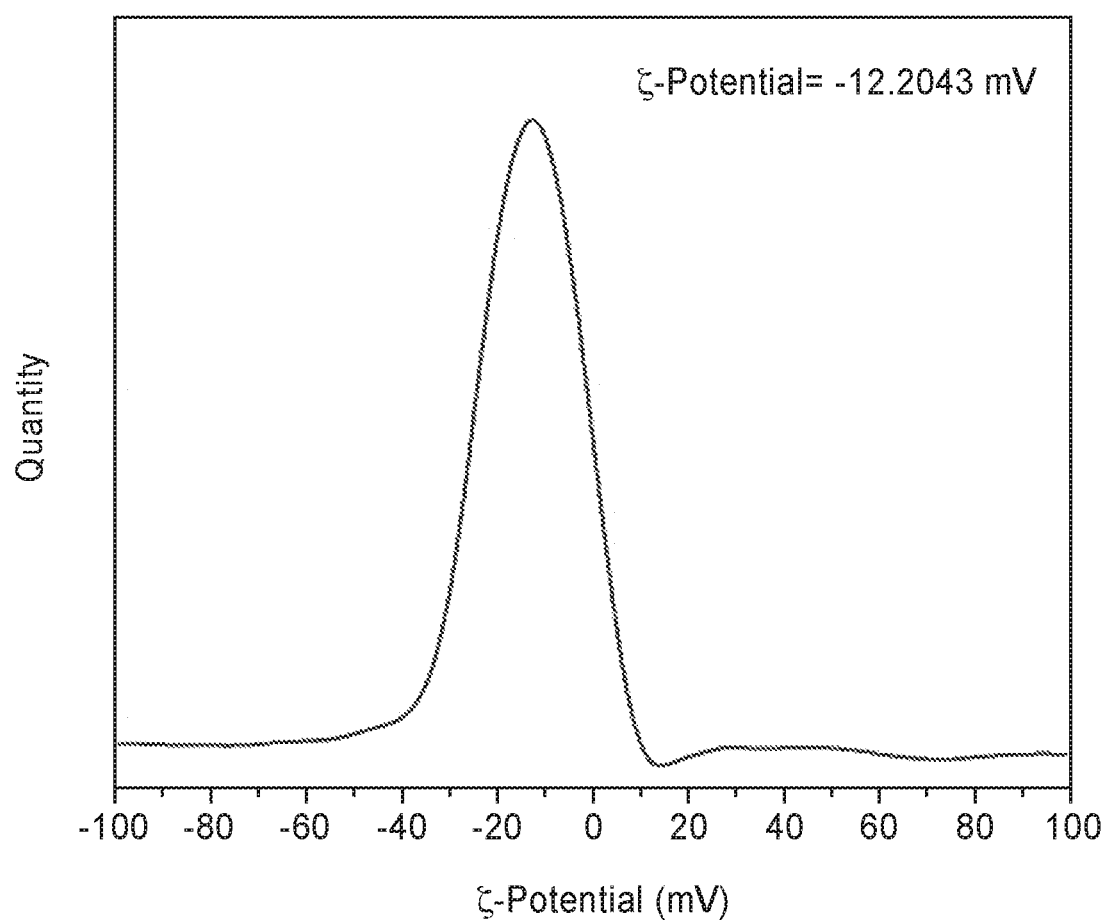
FIG. 1B is a graph depicting the size distribution for the PEO-b-PLA micelles generated using the same test combination (i.e., 6 hours PLA polymerization and sonication in PBS) shown in FIG. 1A and Example 1.

A new era for genome editing technologies has recently emerged based on the development of sequence-specific nucleases. In particular, such nucleases may be used to generate DNA double strand breaks (DSBs) in precise genomic locations, and cellular repair machinery then exploited to silence or replace nucleotides and/or genes. Targeted editing of nucleic acid sequences is a highly promising approach for the study of gene function and also has the potential to provide new therapies for human genetic diseases.

Current gene editing tools include, for example, various enzymes, such as endonucleases, and mobile genetic elements, such as transposons.

The these tools provide the potential, for example, to remove, replace, or add nucleotide bases to native DNA in order to correct or induce a point mutation, as well as to change a nucleotide base in order to correct or induce a frame shift mutation. Further, such tools may enable removing, inserting or modifying pieces of DNA containing a plurality of codons as part of one or more gene(s).

Currently, mechanisms for delivering proteins and/or nucleic acids to target cells include using viral vectors. However, viral-based gene delivery has limitations including toxicity, aggregation of the protein and/or nucleic acid, payload size limits, and difficulties with large-scale production, including costs and time.

Progress has been made in the delivery of functional nucleic acids, using both viral vectors (e.g., retrovirus, adenovirus, etc.) and non-viral vectors. For example, wild-type AAV has attracted considerable interest from gene therapy researchers due to a number of features, such as the virus's apparent lack of pathogenicity. It can also infect non-dividing cells and has the ability to stably integrate into the host cell genome at a specific site (designated AAVS 1)

in the human chromosome 19. The feature makes it somewhat more predictable than retroviruses, which present the threat of a random insertion and of mutagenesis, which is sometimes followed by development of a cancer. AAV-based gene therapy vectors form episomal concatemers in the host cell nucleus. In non-dividing cells, these concatemers remain intact for the life of the host cell. In dividing cells, AAV DNA is lost through cell division, since the episomal DNA is not replicated along with the host cell DNA Random integration of AAV DNA into the host genome is detectable but occurs at very low frequency. AAVs also present very low immunogenicity, seemingly restricted to generation of neutralizing antibodies, while they induce no clearly defined cytotoxic response. These features, along with the ability to infect quiescent cells, demonstrate that AAVs are dominant over adenoviruses as vectors for human gene therapy. However, the use of viral vectors (including AAVs) is also associated with some disadvantages, in particular the limited size of viral genomes. For example, the AAV genome is only 4.8 kilobase (kb), and therefore is unable to be used for single-vehicle delivery of the multitude of gene editing tools of the various embodiments.

Further drawbacks to the use of viruses to deliver gene editing tools may include targeting only dividing cells, random insertion into the host genome, risk of replication, and possible host immune reaction, as well as limitations on payload size imposed by the viral capsid.

In general, non-viral vectors are typically easy to manufacture, less likely to produce immune reactions, and do not produce replication reactions compared to viral vectors; existing methods are generally ineffective for in vivo introduction of genetic material into cells and have resulted in relatively low gene expression. Specifically, a number of existing non-viral systems have been recently explored for delivery of gene editing tools in the form of proteins and/or nucleic acids to cells. Such system may be broadly classified as: "nanocapsules" in which a slurry of free DNA/RNA/protein is wrapped with polymer peptide; "bioconjugates" (e.g., lipids, synthetic macromolecules, etc.) that target the nucleic acid, including via binding to specific proteins expressed by target cells to enable cellular internalization; and "lipid-based vehicles" (e.g., liposomes, lipid-based nanoparticles, etc.) modified with cationic amphiphilic polymers to self-assemble with the nucleic acids based on charge. Each of these non-viral systems presents its own set of issues with respect to encapsulating either single or a multitude of gene editing tools in a single delivery vehicle. For example, in a nanocapsule system, the structure is highly unstable and may leak its contents into the vasculature after intravenous administration. As such, the capability to achieve intracellular delivery and release of a sufficient quantity of material components necessary for effective gene editing is unlikely. In a bioconjugate system, the use of a vector of sufficient size will expose the protein or nucleic acid directly to nucleases in the blood stream/cytosol and can cause fragmentation and destruction of the payload. In lipid-based vehicles, the charged delivery systems have demonstrated poor loading capacity and difficult release of encapsulated payload.

Polymeric micelles have been extensively studied for their potential applications in the drug delivery field. Polymeric micelles are formed by amphiphilic block copolymers, which can self-assemble into nano-sized core/shell structures in an aqueous environment via hydrophobic or ion pair interactions between polymer segments. Such micelles generally are able to solubilize the insoluble drugs, avoid non-selective uptake by the reticuloendothelial system (RES), and utilize the enhanced permeability and retention (EPR) effect for passive targeting. In this manner, a drug's solubility and pharmacokinetic profiles may be significantly improved through the use of micelles.

Polymeric micelles used for drug delivery have in some cases shown capabilities in attenuating nonspecific toxicities and enhancing drug delivery to desired sites resulting in improved therapeutic efficacy. Synthetic amphiphilic copolymers may be beneficial tools for drug delivery because they are highly versatile in terms of composition and architecture. Further, micelles may be customized, for example, by modifying the hydrophilic block using functional groups. Such functional group may include, for example, targeting ligands, such as monoclonal antibody, or intracellular drug delivery moieties, such as cell-penetrating peptides (CPPs), etc.

While nanoparticles have been reported to accumulate preferably in certain regions due to passive and/or active targeting, their inefficient drug release can be another barrier that may significantly lower drug's efficacy. For example, surface PEO chains may inhibit the cellular uptake of long circulating nanoparticles following intracellular events. Therefore, quicker and more controllable payload release remains a target for nanoparticle systems such as micelles.

Therefore, an effective vehicle for delivering nucleic acids, such as mRNA and/or large DNA plasmids, to target cells is needed.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination. Further, reference to values stated in ranges includes each and every value within that range.

As used in this specification and the appended claims, the singular forms "a," "an," and "the" include plural referents unless the content clearly dictates otherwise.

The word "plurality" is used herein to mean more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "subject" and "patient" are used interchangeably herein to refer to human patients, whereas the term "subject" may also refer to any animal. It should be understood that in various embodiments, the subject may be a mammal, a non-human animal, a canine and/or a vertebrate.

The term "monomeric units" is used herein to mean a unit of polymer molecule containing the same or similar number of atoms as one of the monomers. Monomeric units, as used in this specification, may be of a single type (homogeneous) or a variety of types (heterogeneous).

The term "polymer" is used according to its ordinary meaning of a macromolecule comprising connected monomeric molecules.

The term "amphiphilic" is used herein to mean a substance containing both polar (water-soluble) and hydrophobic (water-insoluble) groups.

The term "an effective amount" is used herein to refer to an amount of a compound, material, or composition effective to achieve a particular biological result such as, but not limited to, biological results disclosed, described, or exemplified herein. Such results may include, but are not limited to, the effective reduction of symptoms associated with any of the disease states mentioned herein, as determined by any means suitable in the art. As recognized by those of ordinary skill in the art, the effective amount of an agent, e.g., a nuclease, an integrase, a transposase, a recombinase, a hybrid protein, a fusion protein, a protein dimer, a complex of a protein (or protein dimer) and a polynucleotide, or a polynucleotide, may vary depending on various factors as, for example, on the desired biological response, the specific allele, genome, target site, cell, or tissue being targeted, and the agent being used.

The term "membrane" is used herein to mean a spatially distinct collection of molecules that defines a two-dimensional surface in three-dimensional space, and thus separates one space from another in at least a local sense.

The term "active agent" is used herein to refer to any a protein, peptide, sugar, saccharide, nucleoside, inorganic compound, lipid, nucleic acid, small synthetic chemical compound, or organic compound that appreciably alters or affects the biological system to which it is introduced.

The term, "vehicle" is used herein to refer to agents with no inherent therapeutic benefit but when combined with an active agent for the purposes of delivery into a cell result in modification of the active agent's properties, including but not limited to its mechanism or mode of in vivo delivery, its concentration, bioavailability, absorption, distribution and elimination for the benefit of improving product efficacy and safety, as well as patient convenience and compliance.

The term "carrier" is used herein to describe a delivery vehicle that is used to incorporate a pharmaceutically active agent for the purposes of drug delivery.

The term "homopolymer" is used herein to refer to a polymer derived from one monomeric species of polymer.

The term "copolymer" is used herein to refer to a polymer derived from two (or more) monomeric species of polymer, as opposed to a homopolymer where only one monomer is used. Since a copolymer consists of at least two types of constituent units (also structural units), copolymers may be classified based on how these units are arranged along the chain.

The term "block copolymers" is used herein to refer to a copolymer that includes two or more homopolymer subunits linked by covalent bonds in which the union of the homopolymer subunits may require an intermediate non-repeating subunit, known as a junction block. Block copolymers with two or three distinct blocks are referred to herein as "diblock copolymers" and "triblock copolymers," respectively.

The term "loading capacity" is used herein to refer to the weight of a particular compound within a carrier divided by the total weight of carrier. The terms "complexation efficiency" and "loading efficiency" are interchangeably used herein to refer to the weight a particular compound that is complexed with and/or incorporated within a carrier suspension divided by the weight of the original compound in solution prior to forming a complex (expressed as a %).

The terms "nucleic acid" and "nucleic acid molecule" are used interchangeably herein to refer to a compound with a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester or a phosphorothioate linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone including a phosphorothioate linkage. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propyny 1-uridine, C5-propyny 1-cytidine, C5-methy lcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "nuclease" is used interchangeably herein to refer to an enzyme that forms a complex with (e.g., binds or associates with) one or more nucleic acid to provide a target for cleavage, or indirect guide to another site for cleavage.

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

In order to develop nanoparticles with controllable release, micellar systems with triggered release mechanisms may be developed that enable the delivery drugs or other treatment agents in response to specific stimuli. In particular, pH-sensitive polymeric micelles may be useful therapeutic agents since changes in pH occur in a variety of cellular processes and locations. For example, once the micelle enters cells via endocytosis where pH can drop as low as 5.5-6.0 in endosomes and 4.5-5.0 in lysosomes.

Poly(histidine) (i.e., poly(L-histidine)), is a pH-sensitive polymer due to the imidazole ring providing an electron lone pair on the unsaturated nitrogen. That is, poly(histidine) has amphoteric properties through protonation-deprotonation.

The various embodiments enable intracellular delivery of gene editing tools by complexing with poly(histidine)-based micelles. In particular, the various embodiments provide triblock copolymers made of a hydrophilic block, a hydrophobic block, and a charged block. In some embodiments, the hydrophilic block may be poly(ethylene oxide) (PEO), and the charged block may be poly(L-histidine). An example tri-block copolymer that may be used in various embodiments is a PEO-b-PLA-b-PHIS, with variable numbers of repeating units in each block varying by design. The gene editing tools may be various molecules that are recognized as capable of modifying, repairing, adding and/or silencing genes in various cells.

The correct and efficient repair of double-strand breaks (DSBs) in DNA is critical to maintaining genome stability in cells. Structural damage to DNA may occur randomly and unpredictably in the genome due to any of a number of intracellular factors (e.g., nucleases, reactive oxygen species, etc.) as well as external forces (e.g., ionizing radiation, ultraviolet (UV) radiation, etc.). In particular, correct and efficient repair of double-strand breaks (DSBs) in DNA is critical to maintaining genome stability. Accordingly, cells naturally possess a number of DNA repair mechanisms, which can be leveraged to alter DNA sequences through controlled DSBs at specific sites. Genetic modification tools may therefore be composed of programmable, sequence-specific DNA-binding modules associated with a nonspecific DNA nuclease, introducing DSBs into the genome. For example CRISPR, mostly found in bacteria, are loci containing short direct repeats, and are part of the acquired prokaryotic immune system, conferring resistance to exogenous sequences such as plasmids and phages. RNA-guided endonucleases are programmable genetic engineering tools that are adapted from the CRISPR/CRISPR-associated protein 9 (Cas9) system, which is a component of prokaryotic innate immunity.

Diblock copolymers that may be used as intermediates for making triblock copolymers of the embodiment micelles may have hydrophilic biocompatible poly(ethylene oxide) (PEO), which is chemically synonymous with PEG, coupled to various hydrophobic aliphatic poly(anhydrides), poly(nucleic acids), poly(esters), poly(ortho esters), poly(peptides), poly(phosphazenes) and poly(saccharides), including but not limited by poly(lactide) (PLA), poly(glycolide) (PLGA), poly(lactic-co-glycolic acid) (PLGA), poly(ε-caprolactone) (PCL), and poly (trimethylene carbonate) (PTMC). Polymeric micelles comprised of 100% PEGylated surfaces possess improved in vitro chemical stability, augmented in vivo bioavailability, and prolonged blood circulatory half-lives. For example, aliphatic polyesters, constituting the polymeric micelle's membrane portions, are degraded by hydrolysis of their ester linkages in physiological conditions such as in the human body. Because of their biodegradable nature, aliphatic polyesters have received a great deal of attention for use as implantable biomaterials in drug delivery devices, bioresorbable sutures, adhesion barriers, and as scaffolds for injury repair via tissue engineering.

In various embodiments, molecules required for gene editing (i.e., gene editing tools) may be delivered to cells using one or more micelle formed from self-assembled triblock copolymers containing poly(histidine). The term "gene editing" as used herein refers to the insertion, deletion or replacement of nucleic acids in genomic DNA so as to add, disrupt or modify the function of the product that is encoded by a gene. Various gene editing systems require, at a minimum, the introduction of a cutting enzyme (e.g., a nuclease or recombinase) that cuts genomic DNA to disrupt or activate gene function.

Further, in gene editing systems that involve inserting new or existing nucleotides/nucleic acids, insertion tools (e.g. DNA template vectors, transposable elements (transposons or retrotransposons) must be delivered to the cell in addition to the cutting enzyme (e.g. a nuclease, recombinase, integrase or transposase). Examples of such insertion tools for a recombinase may include a DNA vector. Other gene editing systems require the delivery of an integrase along with an insertion vector, a transposase along with a transposon/retrotransposon, etc. In some embodiments, an example recombinase that may be used as a cutting enzyme is the CRE recombinase. In various embodiments, example integrases that may be used in insertion tools include viral based enzymes taken from any of a number of viruses including, but not limited to, AAV, gamma retrovirus, and lentivirus. Example transposons/retrotransposons that may be used in insertion tools include, but are not limited to, the piggyBac transposon, Sleeping Beauty transposon, and the L1 retrotransposon.

In various embodiments, nucleases that may be used as cutting enzymes include, but are not limited to, Cas9, transcription activator-like effector nucleases (TALENs) and zinc finger nucleases.

In various embodiments, the gene editing systems described herein, particularly proteins and/or nucleic acids, may be complexed with nanoparticles that are poly(histidine)-based micelles. In particular, at certain pHs, poly(histidine)-containing triblock copolymers may assemble into a micelle with positively charged poly(histidine) units on the surface, thereby enabling complexing with the negatively-charged gene editing molecule(s). Using these nanoparticles to bind and release proteins and/or nucleic acids in a pH-dependent manner may provide an efficient and selective mechanism to perform a desired gene modification.

In particular, this micelle-based delivery system provides substantial flexibility with respect to the charged materials, as well as a large payload capacity, and targeted release of the nanoparticle payload. In one example, site-specific cleavage of the double stranded DNA may be enabled by delivery of a nuclease using the poly(histidine)-based micelles.

The various embodiments enable intracellular delivery of gene editing tools by complexing with poly(histidine)-based micelles. In particular, the various embodiments provide triblock copolymers made of a hydrophilic block, a hydrophobic block, and a charged block. In some embodiments, the hydrophilic block may be poly(ethylene oxide) (PEO), and the charged block may be poly(L-histidine). An example tri-block copolymer that may be used in various embodiments is a PEO-b-PLA-b-PHIS, with variable numbers of repeating units in each block varying by design. Without wishing to be bound by a particular theory, it is believed that believed that in the micelles that are formed by the various embodiment triblock copolymers, the hydrophobic blocks aggregate to form a core, leaving the hydrophilic blocks and poly(histidine) blocks on the ends to form one or more surrounding layer.

In various embodiments, poly(histidine)-based micelles may be formed at a pH higher than the pKa of poly (histidine) (e.g., pH of about 7). At a pH of around 6, the amine groups of the poly(histidine) block may be protonated, imparting a positive charge and enabling the poly (histidine) block to complex with negatively charged molecules (e.g., proteins and nucleic acids). If the pH is dropped substantially, such as a pH of around 3-4, the bound protein and/or nucleic acid may be released due to protonation of the poly(histidine). Various applications of the embodiment poly(histidine)-based micelles may exploit the controllable pH-dependent release of the payload molecules to target particular cells and/or pathways.

Additional applications of the embodiment micelles may include conjugating molecules to the hydrophilic block in order to target particular cell types. For example, Apolipoprotein E or N-Acetylgalactosamine (GalNAc) may be conjugated to a PEO block for specific targeting of the micelles to hepatocytes.

The particular methods of creating the block copolymers used in the various embodiments, as well as the techniques of forming the micelles, may be varied based on the composition. In particular, these methods and techniques may be optimized to achieve the most desirable block and nanoparticle properties. For example, the polymerization times may be altered to change the molecular weight of a block, and therefore the overall nanoparticle size, as described in further detail in the examples below.

In various embodiments, the hydrophobic block of the triblock copolymers used to form the micelles may be a polyester, a polyanhydride, a polypeptide, or an artificial polynucleic acid. For example, the hydrophobic block may be an aliphatic polyester, including, but not limited to, poly(lactic acid), poly(glycolic acid) (PGA), poly(lactic-co-glycolic acid) (PLGA), poly(ε-caprolactone) (PCL), and/or poly(3-hydroxybutyrate) (PHB).

Various embodiments may be DNA-based systems that are complexed with the poly(histidine)-based micelles. In some embodiments, an expression vector that expresses a nuclease or other protein may be complexed with poly (histidine)-based micelles. The expression vector may be, for example, a plasmid constructed to contain DNA encoding nuclease as well as a promoter region. Once inside the target cell, the DNA encoding the nuclease may be transcribed and translated to create the enzyme.

Various embodiment systems may also be designed to integrate DNA into the genome of a target cell using a transposon provided on a vector, such as an artificially constructed plasmid. Applications of such systems may include introducing (i.e., "knocking in") a new gene to perform a particular function through the inserted DNA, or inactivating (i.e., "knocking out") a mutated gene that is functioning improperly through interruption in the target DNA.

In some embodiments, the DNA may be transposon that is directly transposed between vectors and chromosomes via a "cut and paste" mechanism. In some embodiments, the transposon may be a retrotransposon, e.g., a DNA that is first transcribed into an RNA intermediate, followed by reverse transcription into the DNA that is transposed.

In various embodiments, the poly(histidine)-based micelles may complex with a vector that includes the transposon, as well as a transposase that catalyzes the integration of the transposon into specific sites in the target genome. The transposase that is used is specific to the particular transposon that is selected, each of which may have particular properties are desirable for use in various embodiments. One example transposon is the piggyBac transposon, which is transposed into a target genome by the piggyBac transposase. Specifically, the piggyBac transposase recognizes transposon-specific inverted terminal repeat sequences (ITRs) on the ends of the transposon, and moves the contents between the ITRs into TTAA chromosomal sites. The piggyBac transposon system has no payload limit for the genes of interest that can be included between the ITRs. Another example transposon system is the sleeping beauty transposon, which is transposed into the target genome by the sleeping beauty transposase that recognizes ITRs, and moves the contents between the ITRs into TA chromosomal sites. In various embodiments, SB transposon-mediated gene transfer, or gene transfer using any of a number of similar transposons, may be used for long-term expression of a therapeutic gene.

Similar to the RNA-directed nucleases discussed here, poly(histidine)-based micelles may complex with the transposase in its native protein for, as mRNA that is transcribed into protein in the target cell, or as an expression vector containing DNA to express the transposase protein. For example, genes encoding the transposase may be provided in the same vector as the transposon itself, or on a different vector.

Various embodiments may further enable complexing a nuclease and a transposon system in a poly(histidine)-based micelles for delivery to a target cell. Such micelle systems may be used for example, to replace a mutated gene that causes disease with a healthy copy of the gene that is inserted at a specific site dictated by the activity of the nuclease. Specifically, a transposon may be created that includes one or more gene to be inserted, which is surrounded by the ITRs for recognition by the transposase. The transposon and ITRs may be provided on a vector that contains homology arms on each end of the ITRs. The transposon system (i.e., the transposon vector and corresponding transposase), when delivered with the nuclease, may serve the function of the DNA repair template used in HDR. That is, following the creation of one or more DSB by the nuclease, the transposon may be inserted into the target DNA based on the homology arms. In some embodiments, the transposon insertion may occur between the two ends generated by a DSB. In other embodiments, the transposon may be inserted between one arm of a first DSB and the other arm at a second DSB in the target DNA (i.e., replacing the sequence between two DSBs).

While a variety poly(histidine)-based micelle formulations that complex with proteins and/or nucleic acids may be designed for different uses, each complexing system may include common characteristics in order to be effective. For example, nucleic acids may be complexed with poly(histidine)-based micelles with at least 40% efficiency. Such minimum efficiency ensures delivery of enough active molecule to achieve efficient DNA cleavage and/or other modification, and that the product can be reproducibly generated at a low cost. In another example, the poly(histidine)-based micelles may be designed to be stable, yet to provide facile release of the complexed payload once the micelle has been taken up intracellularly, thereby avoiding endosomal retrafficking and ensuring release of the nucleic acids. Moreover, in various gene therapy systems, the vector (i.e., transposon) may be designed to provide stable expression.

The gene editing tools provided in the poly(histidine)-based micelles described herein may be beneficial for a number of in vivo applications. For example, the embodiment materials may be delivered to various cell types in order to cut or to repair gene defects. Such cells include, but are not limited to, hepatocytes, hepatic endothelial cells, immune cells, neurons, etc. The embodiment poly(histidine)-based micelles may also be delivered to various cell types in order to silence defective genes that cause diseases (for example, delivery to retinal cells to silence mutations underlying Leber's Congenital Amaurosis).

Various methods may be used to generate the poly(histidine)-based micelles and/or complexation of micelles and proteins and/or nucleic acids described herein. In some embodiments, conventional preparation techniques such as thin-film rehydration, direct-hydration, and electro-formation may be used to form polymeric micelles that complex with nucleic acids and/or proteins with gene editing functions into various degradable and non-degradable micelles.

Creation of various poly(histidine)-based micelles complexed with model proteins and model nucleic acids may be created using conventional techniques. For example, bovine serum albumin (BSA; Mw=about 66 kDa), which has a size and thermal stability (i.e., denaturation above 60° C.) comparable to other medium size proteins with therapeutic potential, was used as a model protein. Other model proteins that may be used in such compositions are myoglobin (Mb; Mw=about 17 kDa) and catalase (Mw=about 250 kDa). The complexing of model proteins having various sizes provides a range of sizes of functional proteins that may be used in various embodiments. Further, various DNA plasmids may be used as model nucleic acids for poly(histidine)-based micelles, such as plasmid DNA encoding the mammalian expression vector for expression of green fluorescent protein (GFP) using the elongation factor I alpha (EF la) promoter) (i.e., pEF-GFP DNA). The pEF-GFP DNA is about 5000 base-pairs, and has a molecular weight of about 3283 kDa.

In the micelles that are formed by the various embodiment triblock copolymers, the hydrophobic blocks may aggregate to form a core, leaving the hydrophilic blocks and poly(histidine) blocks on the ends to form one or more surrounding layer.

EXAMPLES

Different micelle formulations may be used to compare the properties between resulting particles. For example, poly(histidine)-containing triblock copolymers are used to form micelles that complex with negatively charged particles, including nucleic acids and some proteins.

Details about comparative and quantitative studies that were performed are provided below.
Experimental Procedures
Formation and Characterization of Polymeric Micelles.
PEO-b-PLA-b-PHIS micelles were prepared by a thin-film rehydration method.
In overview, 20 mg of polymer was dissolved in 1 mL of DCM. The organic solvent was evaporated to form a polymer thin film by flushing Nitrogen gas. The polymer thin film was rehydrated in PBS and particles were formed by 30 minutes ice-water bath sonication at 30 kHz. Particle sizes and zeta potentials were measured using a Delsa Nano Submicron Particle Size and Zeta Potential Analyzer (Beckman Coulter).

Complexation of Protein or DNA with Polymeric Micelles:

Suspensions of polymeric micelles were diluted with Opti-MEM Media® (Invitrogen) to different concentrations, varying the final numbers of amino groups in solution. Equal volume solutions containing protein or DNA where then added to the micelles. For DNA, the primary parameters that were varied included the initial ratios of free amines to phosphates (NIP) in suspension, which ranged from 5:1 to 40:1. Protein- or DNA-complexed micelles were then formed by gentle pipetting and allowed to equilibrate for 30 min at RT. To determine the maximal loading of protein/DNA, the efficiency of micellar complexation, and the rates of release within different pH solutions, the micro-BSA assay (for protein concentrations), a fluorescence standard curve (for flurophore-conjugated protein), and/or ICP-MS was utilized (to determine the amount of platinum-bound DNA in solution).

Example 1: Diblock Copolymer Micelle Model

In a first copolymer micelle model, micelles were created using the diblock copolymer PEO-b-PLA. Various time durations for polymerizing the PLA block were tested in combination with different techniques for forming the micelles (i.e., "test combinations"). The of PLA polymerization times, micelle formation techniques, and mean diameter sizes of the resulting nanoparticles are shown in FIG. 1A. As shown, using the particular test combination of PLA polymerization for 6 hours (25 PLA units) and sonication of the copolymers in phosphate-buffered saline (PBS), the mean diameter of the resulting micelles was 247 nm.

Figure 1C:
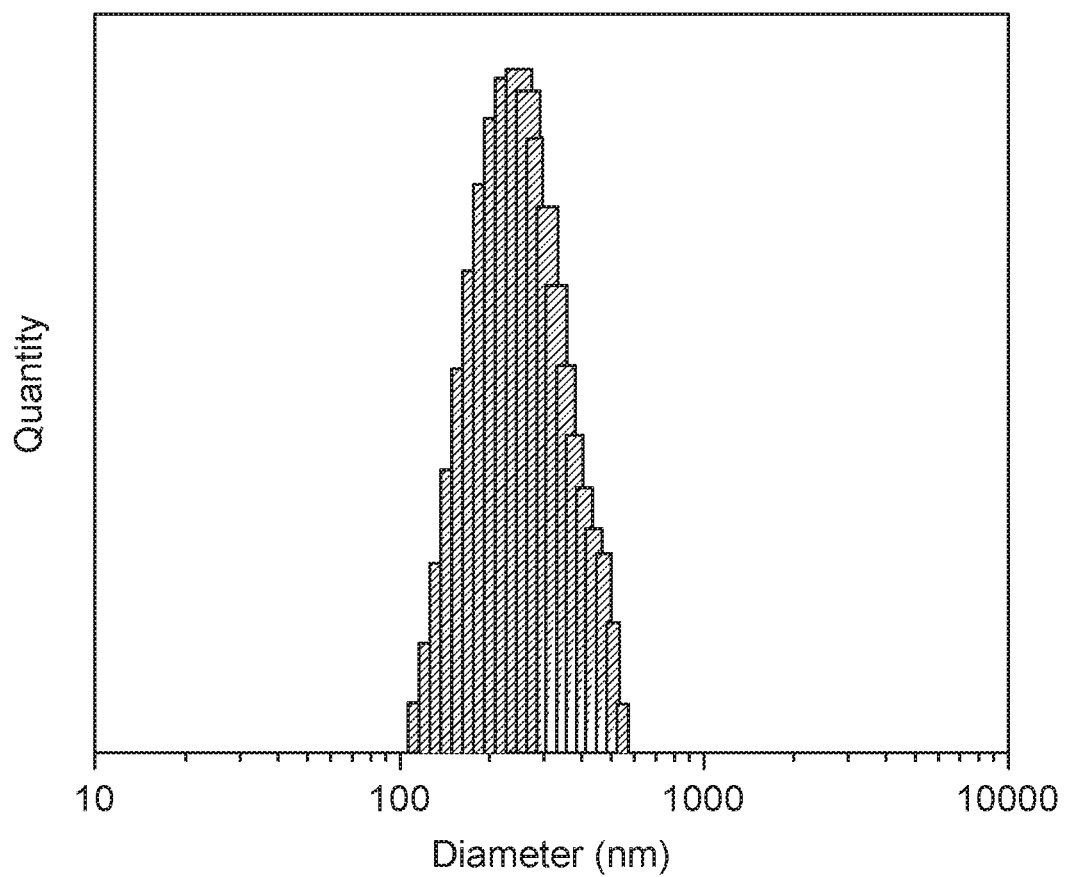
FIG. 1C is a graph showing the ζ-potential distribution of the PEO-b-PLA micelles generated using the same test combination (i.e., 6 hours PLA polymerization and sonication in PBS) shown in FIGS. 1A-B and Example 1. As demonstrated, the ζ-potential of the tested PEO-b-PLA micelle is about −12.20 mV.

As also shown, increasing the amount of time for PLA polymerization resulted in larger mean diameters of the resulting nanoparticles. FIG. 1B is graph showing the size distribution for the PEO-b-PLA micelles generated using the same test combination (i.e., 6 hours PLA polymerization and sonication in PBS). FIG. 1C is a graph showing the ζ-potential distribution of the PEO-b-PLA micelles generated using the same test combination (i.e., 6 hours PLA polymerization and sonication in PBS). As demonstrated, the ζ-potential of the tested PEO-b-PLA micelle is about −12.20 mV.

Figure 2:
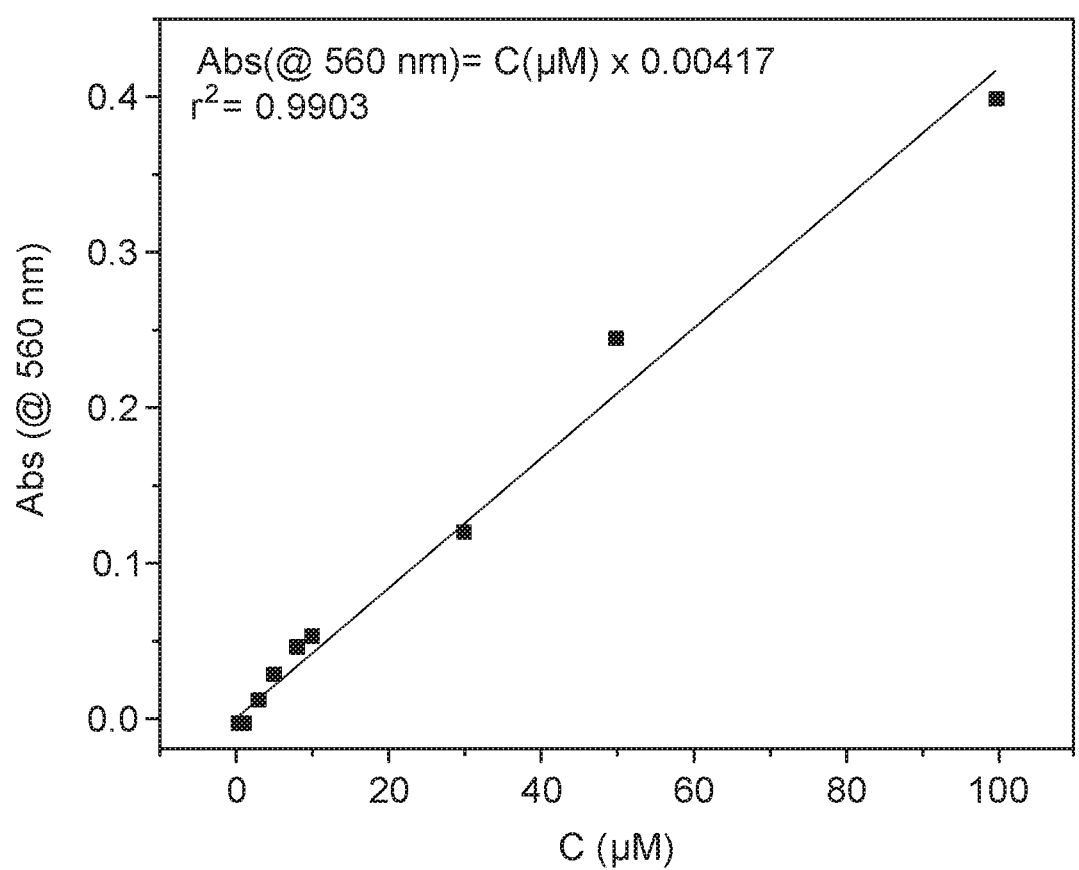
FIG. 2 is a graph depicting the absorbance of light at a wavelength of 560 nm by the micelles with different concentrations of the DIL dye in solution. In particular, the graph may be used to quantify how much DIL dye can be bound to the hydrophobic portion of the micelles. Specifically, it was found that 1 mg of the PEO-b-PLA micelles was able to load around 4 μM of the DIL dye.

The block copolymer micelles in the various embodiments may also encapsulate water-insoluble molecules in the hydrophobic block. This capability was shown by encapsulating a lipophilic carbocyanine fluorescent dye (DIL dye) in the hydrophobic portion (i.e., PLA) of the PEO-b-PLA micelles described with respect to FIGS. 1B and 1C (i.e., prepared by 6 hours PLA polymerization and sonication in PBS). FIG. 2 is a graph showing the absorbance of light at a wavelength of 560 nm by the micelles with different concentrations of the DIL dye in solution. In particular, the graph may be used to quantify how much DIL dye can be bound to the hydrophobic portion of the micelles. Specifically, it was found that 1 mg of the PEO-b-PLA micelles was able to load around 4 μM of the DIL dye.

In various embodiments, creating a triblock copolymer for use in micelle formation involves attaching a poly(histidine) block to a diblock copolymer that has a hydrophobic and a hydrophilic block. The poly(histidine) block may be attached to the hydrophobic block, such that the resulting polymer contains the hydrophobic block in between a hydrophilic block and the poly(histidine) block.

Figure 3B:
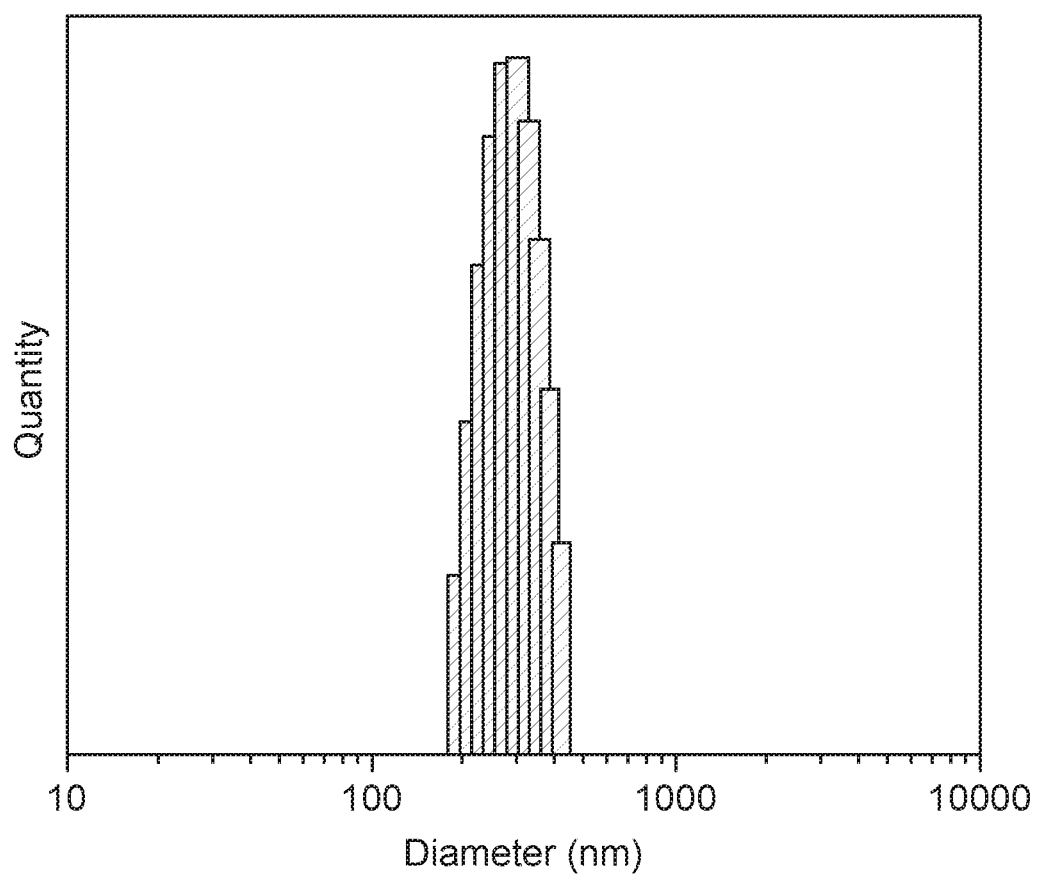
FIG. 3B is graph showing the size distribution (around 248 nm in diameter) for the PEO-b-PLA-b-PHA micelles generated using the same preparation parameters (i.e., 6 hours PLA polymerization, 48 hours PHIS polymerization, and THS in DCM).
Figure 3C:
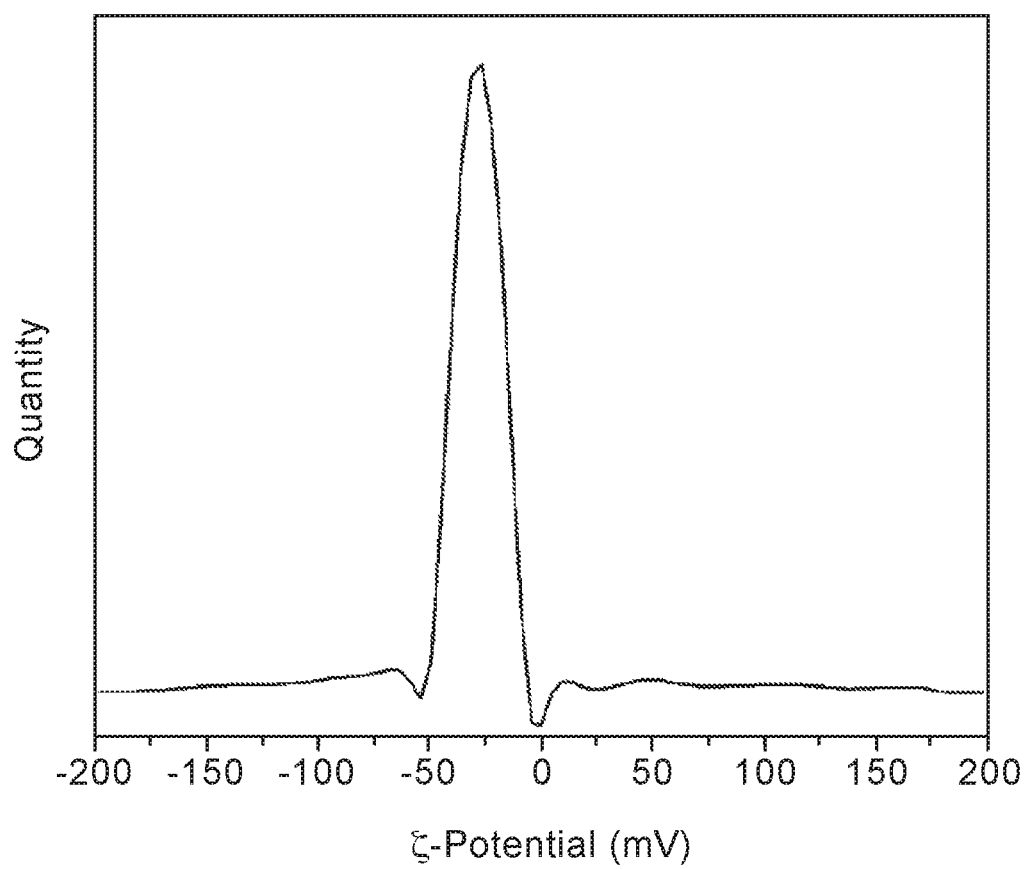
FIG. 3C is a graph of the ζ-potential distribution of the PEO-b-PLA-b-PHIS micelles generated using the same preparation parameters (i.e., 6 hours PLA polymerization, 48 hours PHIS polymerization, and THS in DCM). As demonstrated, the ζ-potential of the tested PEO-b-PLA-b-PHIS micelle is about −18 mV.

In an embodiment, poly(histidine)-based micelles were created using the triblock copolymer PEO-b-PLA-b-PHIS. As described above with respect to FIGS. 1B and 2, creating the PEO-b-PLA portion of the copolymers involved PLA polymerization for 6 hours, and sonicating the diblock copolymers in PBS. Various time durations for creating the poly(histidine) block and adding it to the PEO-b-PLA copolymer were used in combination with different techniques for forming the triblock copolymer micelles. The PHIS polymerization times, micelle formation techniques, and mean diameter sizes of the resulting nanoparticles are shown in FIG. 3A. Using the particular combination of PHIS polymerization for 48 hours and thin film rehydration (TFR) of the block copolymers in dichloromethane (DCM) of the copolymers in PBS, the mean diameter of the resulting micelles was 248 nm. FIG. 3B is graph showing the size distribution (around 248 nm in diameter) for the PEO-b-PLA-b-PHA micelles generated using the same preparation parameters (i.e., 6 hours PLA polymerization, 48 hours PHIS polymerization, and THS in DCM). FIG. 3C is a graph of the ζ-potential distribution of the PEO-b-PLA-b-PHIS micelles generated using the same preparation parameters (i.e., 6 hours PLA polymerization, 48 hours PHIS polymerization, and THS in DCM). As demonstrated, the ζ-potential of the tested PEO-b-PLA-b-PHIS micelle is about −18 mV.

FIG. 4 is a chart showing the variation in properties of the PEO-b-PLA-b-PHIS micelles in different pHs was tested. As shown, the micelles were the smallest at a pH of around 7, with a mean diameter size of around 316 nm. When the pH was substantially raised or lowered, the mean diameter size increases. At the lower pH, such increase is likely due to the micelle swelling based on poly(histidine) chains gaining positive charges and growing.

To demonstrate the capability of poly(histidine)-based micelles to complex with negatively charged proteins, bovine serum albumin (BSA) was added to a solution with PEO-b-PLA-b-PHIS micelles at a low pH (i.e., lower than 6.6). In this manner, the BSA may complex with positively charged PHIS blocks, thereby creating neutrally charged nanoparticle-protein complexes.

When the BSA was added at a ratio of 1:3 polymer-to-protein, the complexation efficiency was around 50%. Without wishing to be bound by a particular theory, it is believe that the micelle core was formed by the hydrophobic PLA blocks. It is also believed that the BSA complexed with the poly(histidine) created a "shell" layer on the surface of the PLA core, while the PEO created a dispersed second "shell" layer around the BSA/poly(histidine) layer.

To demonstrate the capability of poly(histidine)-based micelles to complex with a nucleic acid, a model plasmid DNA encoding the mammalian DNA vector for expression of green fluorescent protein (GFP) using the elongation factor 1 alpha (EF1a) promoter (i.e., pEF-GFP DNA) was added to a solution with PEO-b-PLA-b-PHIS micelles at a low pH (i.e., lower than 6.6). Similar to BSA, the pEF-GFP DNA may complex with positively charged PHIS blocks, thereby creating neutrally charged nanoparticle-DNA complexes.

Without wishing to be bound by a particular theory, it is believe that the micelle cores were formed by the hydrophobic PLA blocks. It is also believed that the BSA or pEF-GFP complexed with the poly(histidine) created a "shell" layer on the surface of the PLA core, while the PEO created a dispersed second "shell" layer around the BSA/poly(histidine) or pEF-GFP DNA/poly(histidine) layer.

Figure 5:
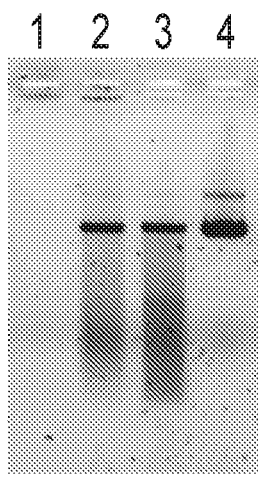
FIG. 5 is a photograph of a gel electrophoresis depicting DNA+mRNA encapsulation and release from PEO-PLA-PHIS particles. 1% agarose gel electrophoresis was used to demonstrate the encapsulation of DNA and mRNA into PEO-PLA-PHIS particles (well 1). Exposure of particles to acidic pH of 4.6 causes protonation of PHIS and disruption of particle conformation to result in plasmid release as observed in the DNA band from well 2 in the gel image. Plasmid release can be also triggered by surfactant exposure from the loading dye containing SDS as can be seen in the well 3. The DNA band from release was compared to the band resulting from running DNA alone in the gel (well 4).

FIG. 5 demonstrates DNA+mRNA encapsulation and release from PEO-PLA-PHIS particles. 1% agarose gel electrophoresis was used to demonstrate the encapsulation of DNA and mRNA into PEO-PLA-PHIS particles (well 1). Exposure of particles to acidic pH of 4.6 causes protonation of PHIS and disruption of particle conformation to result in plasmid release as observed in the DNA band from well 2 in the gel image. Plasmid release can be also triggered by surfactant exposure from the loading dye containing SDS as can be seen in the well 3. The DNA band from release was compared to the band resulting from running DNA alone in the gel (well 4).

Figure 6A:
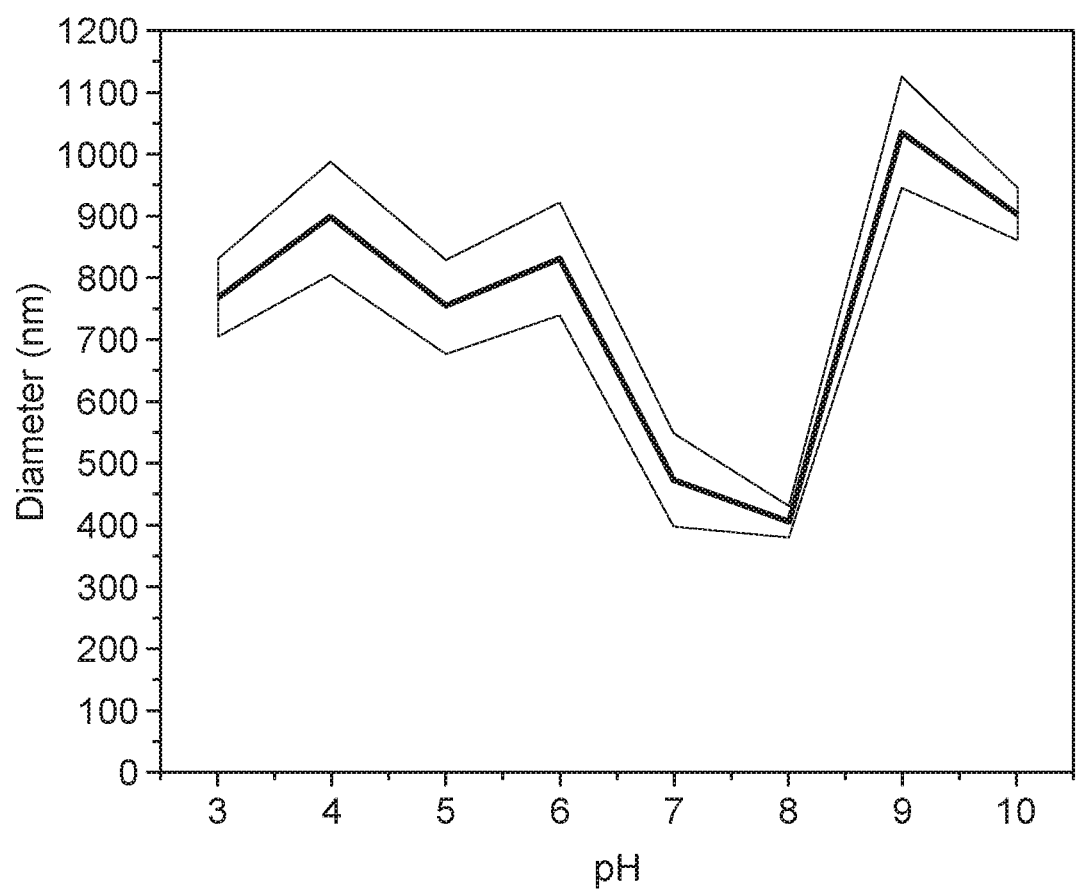
FIG. 6A is a graph of the average diameter of PEO-b-PLA-b-PHIS micelles complexed with BSA as a function of pH as discussed in Example 1.
Figure 6B:
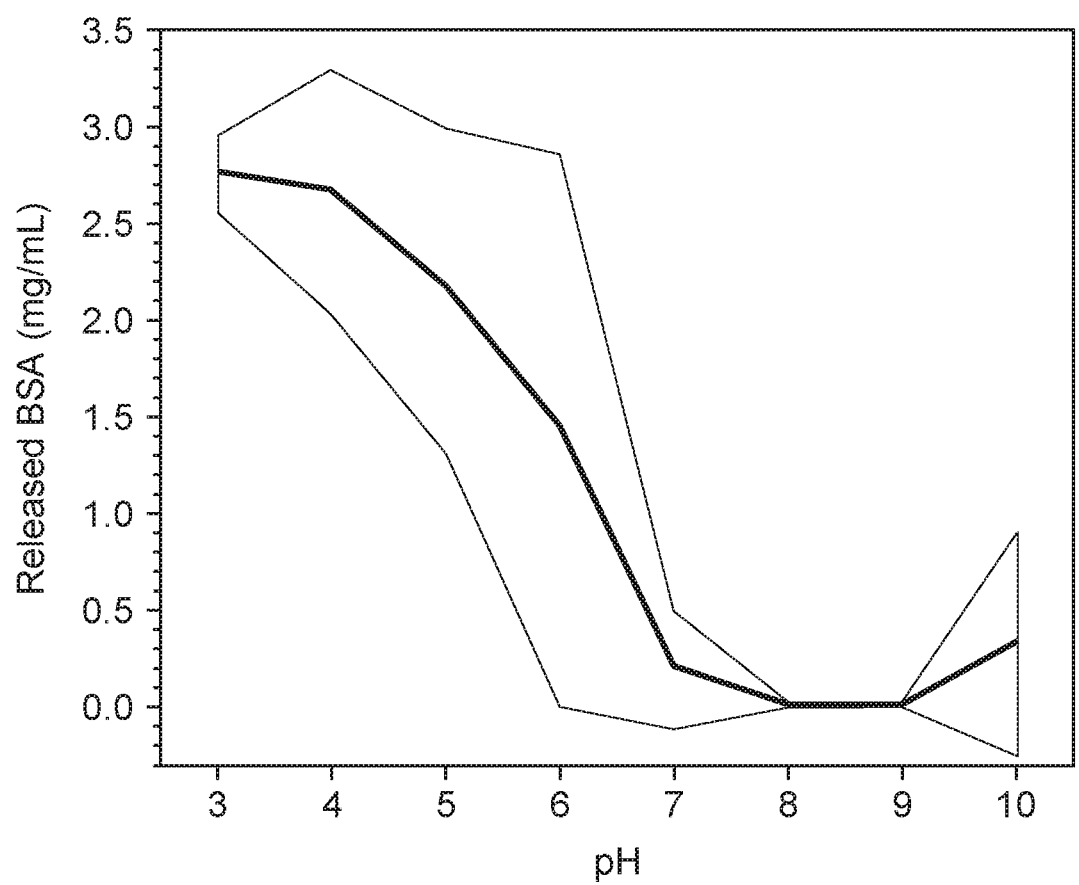
FIG. 6B is a graph of the amount of released BSA as a function of pH as discussed in Example 1.
Figure 8:
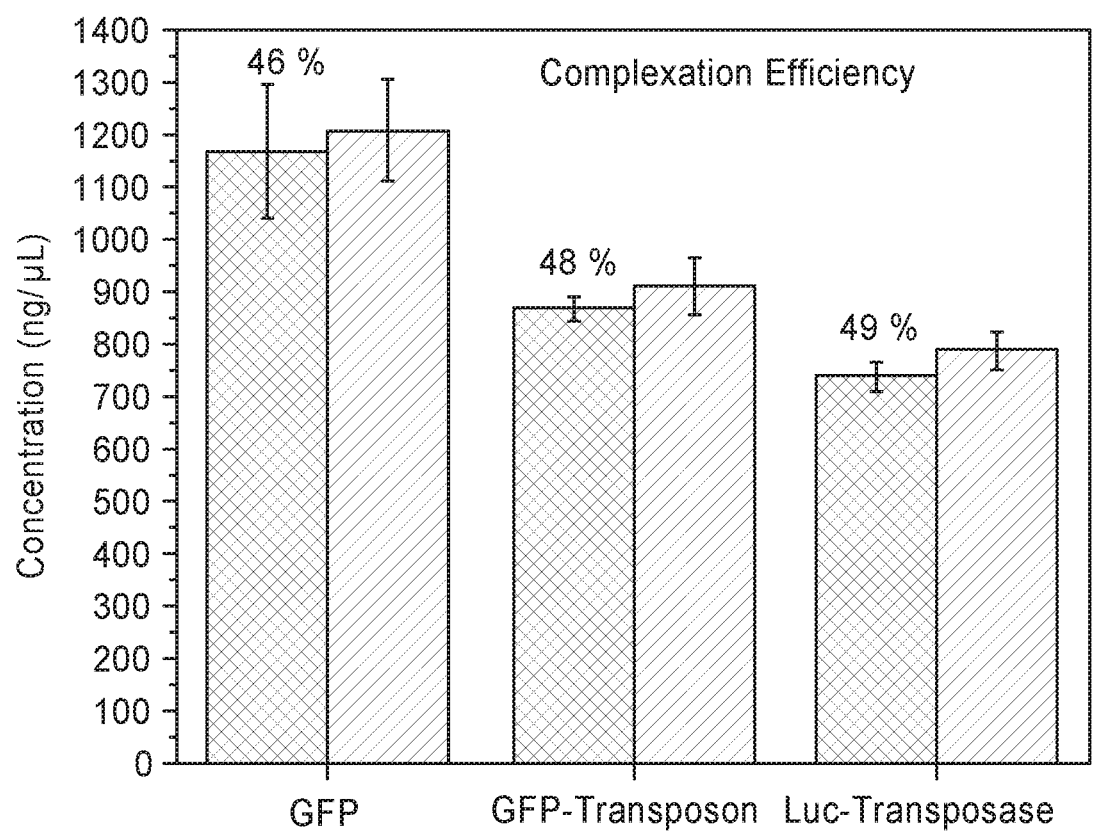
FIG. 8 is a graph depicting piggyBac delivery via polymeric micelles. Evaluation of complexation of PEO-b-PLA-b-PHIS micelles with an pEF-GFP DNA vector (GFP), GFP-piggyBac transposon (GFP-Transposon), which was delivered with a second micelle that was complexed with piggyBac transposase mRNA or a DNA vector containing luciferase on a sleeping beauty transposon as well as the sleeping beauty transposase. Micelles were purified on a GPC column and a second fraction was detected as micelles containing DNA. Molar ratio of polymer to DNA cargo was 20:1.
Figure 9:
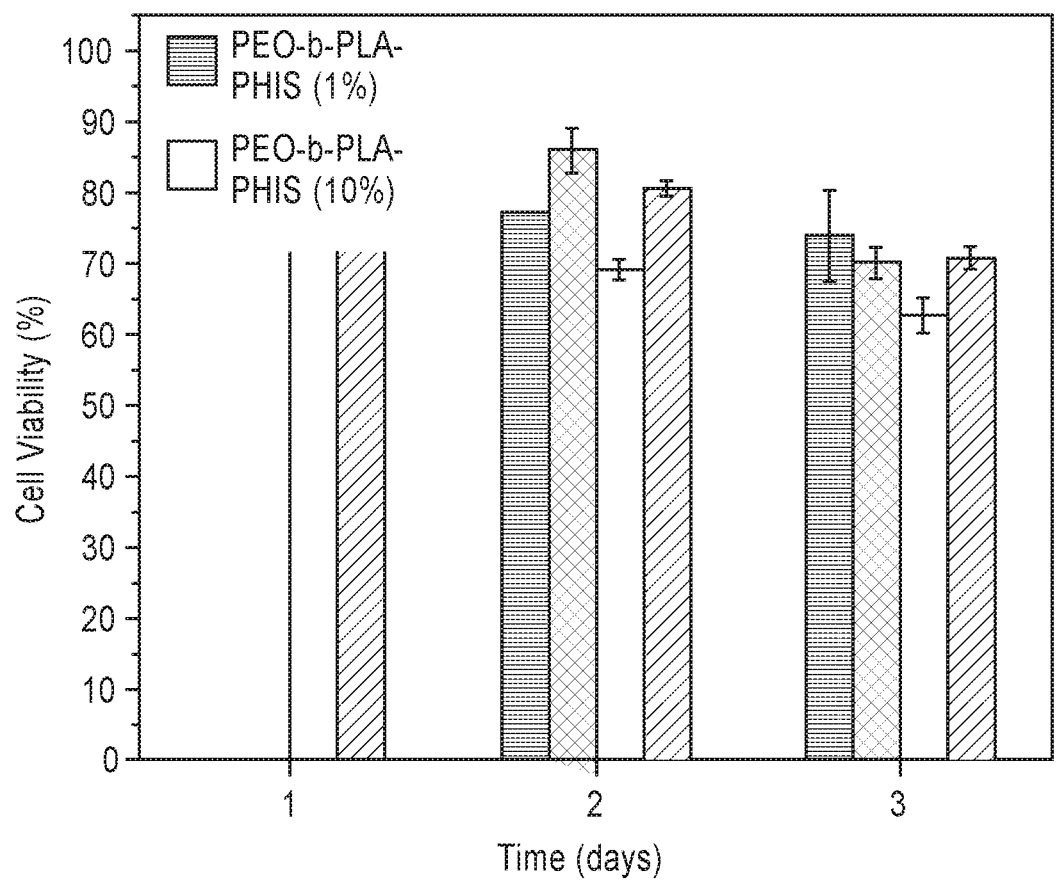
FIG. 9 is a graph depicting piggyBac delivery via polymeric micelles. Evaluation of in vitro toxicity of PEO-b-PLA-b-PHIS micelles at different concentrations. Micelle toxicity in HepG2 cells was evaluated by an MTT assay. Empty micelles were incubated with cells over 3 days at the typical transfection concentration of DNA (1%) and at 10× the typical concentrations (i.e. 10%).

The properties of the poly(histidine)-based micelles complexed with protein and/or nucleic acid also vary based on the pH. FIG. 6A is a graph of the average diameter of PEO-b-PLA-b-PHIS micelles complexed with BSA as a function of pH, and FIG. 6B is a graph of the amount of released BSA as a function of pH.

As shown, the nanoparticles are smallest at a pH of around 7 (around 400 nm). When the pH is raised above 7 (e.g., up to around 10), the overall micelle size also increases, and BSA remains complexed with the micelle. When the pH is lowered below 7 (e.g., to about 3-4), the overall micelle size also increases (e.g., swells), but at a pH of about 3-4, BSA is released from the micelles.

In another example, HepG2 cells were seeded overnight into a 24-well plate at a confluence of 50,000 cells per well. Bare DNA and the different formulations containing DNA were added to the cells to achieve a final concentration of DNA of 5 µg per well. The formulations used were: Lipofectamine (a traditional method in the market used to transfect cells in vitro), PEO-PLA-PHIS particles, and PEO-PLL-PHIS particles. After 2 days of co-incubation, the cells were detached from the surface by trypsin, diluted with PBS and analyzed by flow cytometry. Analysis in flow cytometry was done to measure GFP fluorescence of transfected cells in a cell population of 10,000 cells per sample. Each condition was measured for 5 biological repetitions.

FIG. 7 demonstrates transfection efficiency. HepG2 cells were seeded overnight in 24-well plates at 50,000 cells/well. Cell were exposed to different formulations in Opti-MEM Media (DNA alone, Lipofectamine+DNA+mRNA and PEO-PLA-PHIS+DNA+mRNA) at a final concentration of 500 ng of DNA per well. At 48 hours post-incubation, cells were analyzed for GFP expression by microscopy and flow cytometry to determine the transfection efficiency for each condition.

Further poly(histidine)-containing triblock copolymers using the same protocols have been and continue to be developed. Such copolymers include, in addition to poly (histidine), non-degradable and degradable diblocks such as: degradable polymers include, but are not limited to: PEO (5000)-b-PCL(16300) ("P2350-EOCL"); PEO(2000)-b-PMCL(11900) ("OCL"); PEO(2000)-b-PMCL(8300) ("OMCL"); PEO(1100)-b-PTMC(5100) ("OTMC"); and PEO(2000)-b-PTMC/PCL(11200) ("OTCL").

The various embodiments include a micelle structure containing a triblock copolymer capable of complexing with at least one protein or nucleic acid, the triblock copolymer including a hydrophilic block including poly(ethylene oxide), a hydrophobic block, and a poly(L-histidine) block, wherein the poly(L-histidine) block enables pH-dependent release of the at least one protein or nucleic acid. In an embodiment, the hydrophobic block is selected from the group including poly(esters), poly(anhydrides), poly(peptides), and artificial poly(nucleic acids). In an embodiment, the hydrophobic block includes at least one aliphatic polyester selected from the group of including poly(lactic acid), poly(glycolic acid) (PGA), poly(lactic-co-glycolic acid)

(PLGA), poly(ε-caprolactone) (PCL), and poly(3-hydroxybutyrate) (PHB). In an embodiment, the hydrophobic block includes poly(lactic acid) having an average length of 25 units.

Various embodiments may include a composition for delivering at least one gene editing molecule to a cell, the composition including, a micelle assembled from a plurality of triblock copolymers in which each triblock copolymer having at least one hydrophobic block, at least one hydrophilic block, and at least one poly(L-histidine) block in which the at least one poly(L-histidine) block complexes with the at least one gene editing molecule, and the at least one poly(L-histidine) block is capable of a pH dependent release of the at least one gene editing molecule.

In an embodiment, the at least one gene editing molecule may include one or more protein or nucleic acid encoding for a protein in which the protein is selected from a group that includes transposases, nucleases, and integrases. In an embodiment, the protein may be a nuclease selected from a group that includes CRISPR associated protein 9 (Cas9), transcription activator-like effector nucleases and zinc finger nucleases. In an embodiment, the at least one gene editing molecule may include one or more transposable elements. In an embodiment, the one or more transposable elements may include, but are not limited to, a piggyBac transposon, a Sleeping Beauty transposon, or a LINE-1 (L1) retrotransposon. In an embodiment, the at least one gene editing molecule may further include one or more transposase.

Further embodiments may include a kit including a pharmaceutical composition for delivering at least one gene editing molecule to a cell. The composition may include a micelle assembled from a plurality of triblock copolymers in which each triblock copolymer having at least one hydrophobic block, at least one hydrophilic block, and at least one poly(L-histidine) block in which the at least one poly(L-histidine) block complexes with the at least one gene editing molecule, and the at least one poly(L-histidine) block is capable of a pH dependent release of the at least one gene editing molecule, and an implement for administering the pharmaceutical composition intravenously, via inhalation, topically, per rectum, per the vagina, transdermally, subcutaneously, intraperitoneally, intrathecally, intramuscularly, or orally.

What is claimed is:

1. A composition for delivering at least one gene editing molecule to a cell, the composition comprising:
   a micelle assembled from a plurality of triblock copolymers, wherein each triblock copolymer having at least one hydrophobic block, at least one hydrophilic block, and at least one poly(L-histidine) block,
   wherein:
   the at least one poly(L-histidine) block complexes with the at least one gene editing molecule;
   the at least one poly(L-histidine) block is capable of a pH dependent release of the at least one gene editing molecule;
   the at least one hydrophilic block comprises poly(ethylene oxide) and the at least one hydrophobic block comprises poly(lactic acid); and
   wherein the at least one gene editing molecule comprises one or more of a nucleic acid encoding for a protein, wherein the protein is selected from the group consisting of a transposase, a nuclease and an integrase;
   wherein the molar ratio of triblock copolymers to the at least one gene editing molecule is about 20:1.

2. The composition of claim 1, wherein the nuclease is selected from the group comprising:
   a CRISPR associated protein 9 (Cas9);
   a type IIS restriction enzyme;
   a transcription activator-like effector nuclease (TALEN); and
   a zinc finger nuclease (ZFN).

3. The composition of claim 1, wherein the at least one gene editing molecule further comprises one or more transposable elements.

4. The composition of claim 3, wherein the one or more transposable elements comprise a piggyBac transposon, a Sleeping Beauty transposon or a LINE-1 (L1) transposon.

5. The composition of claim 1, wherein the protein is a transposase.

6. A kit, comprising:
   a pharmaceutical composition comprising the composition of claim 1; and
   an implement for administering the pharmaceutical composition intravenously, via inhalation, topically, per rectum, per the vagina, transdermally, subcutaneously, intraperitoneally, intrathecally, intramuscularly or orally.

7. A composition for delivering at least one gene editing molecule to a cell, the composition comprising:
   a micelle assembled from a plurality of triblock copolymers, wherein each triblock copolymer having at least one hydrophobic block, at least one hydrophilic block, and at least one poly(L-histidine) block,
   wherein:
   the at least one poly(L-histidine) block complexes with the at least one gene editing molecule;
   the at least one poly(L-histidine) block is capable of a pH dependent release of the at least one gene editing molecule;
   the at least one hydrophilic block comprises poly(ethylene oxide) and the at least one hydrophobic block comprises poly(lactic acid); and
   wherein the at least one gene editing molecule comprises one or more of a protein, wherein the protein is selected from the group consisting of a transposase, a nuclease and an integrase;

wherein the molar ratio of triblock copolymers to the at least one gene editing molecule is about 2:3.

8. The composition of claim 7, wherein the nuclease is selected from the group comprising:
   a CRISPR associated protein 9 (Cas9);
   a type IIS restriction enzyme;
   a transcription activator-like effector nuclease (TALEN); and
   a zinc finger nuclease (ZFN).

9. The composition of claim 7, wherein the at least one gene editing molecule further comprises one or more transposable elements.

10. The composition of claim 9, wherein the one or more transposable elements comprise a piggyBac transposon, a Sleeping Beauty transposon or a LINE-1 (L1) transposon.

11. The composition of claim 7, wherein the protein is a transposase.

12. A kit, comprising:
   a pharmaceutical composition comprising the composition of claim 7; and
   an implement for administering the pharmaceutical composition intravenously, via inhalation, topically, per rectum, per the vagina, transdermally, subcutaneously, intraperitoneally, intrathecally, intramuscularly or orally.

* * * * *

SEQUENCE LISTING

```
<160> NUMBER OF SEQ ID NOS: 4

<210> SEQ ID NO 1
<211> LENGTH: 1053
<212> TYPE: PRT
<213> ORGANISM: Artificial Sequence
<220> FEATURE:
<223> OTHER INFORMATION: dSaCas9

<400> SEQUENCE: 1

Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205
```

```
Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
                260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Ile Ile Arg Thr Thr
            500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Ala Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
```

```
                625                 630                 635                 640
            Phe Ile Asn Arg Asn Leu Val Asp Thr Arg Tyr Ala Thr Arg Gly Leu
                            645                 650                 655

Met Asn Leu Leu Arg Ser Tyr Phe Arg Val Asn Asn Leu Asp Val Lys
                        660                 665                 670

Val Lys Ser Ile Asn Gly Gly Phe Thr Ser Phe Leu Arg Arg Lys Trp
                            675                 680                 685

Lys Phe Lys Lys Glu Arg Asn Lys Gly Tyr Lys His His Ala Glu Asp
                        690                 695                 700

Ala Leu Ile Ile Ala Asn Ala Asp Phe Ile Phe Lys Glu Trp Lys Lys
            705                 710                 715                 720

Leu Asp Lys Ala Lys Lys Val Met Glu Asn Gln Met Phe Glu Glu Lys
                            725                 730                 735

Gln Ala Glu Ser Met Pro Glu Ile Glu Thr Gln Glu Tyr Lys Glu
                        740                 745                 750

Ile Phe Ile Thr Pro His Gln Ile Lys His Ile Lys Asp Phe Lys Asp
                            755                 760                 765

Tyr Lys Tyr Ser His Arg Val Asp Lys Lys Pro Asn Arg Glu Leu Ile
                        770                 775                 780

Asn Asp Thr Leu Tyr Ser Thr Arg Lys Asp Asp Lys Gly Asn Thr Leu
            785                 790                 795                 800

Ile Val Asn Asn Leu Asn Gly Leu Tyr Asp Lys Asp Asn Asp Lys Leu
                        805                 810                 815

Lys Lys Leu Ile Asn Lys Ser Pro Glu Lys Leu Leu Met Tyr His His
                            820                 825                 830

Asp Pro Gln Thr Tyr Gln Lys Leu Lys Leu Ile Met Glu Gln Tyr Gly
                        835                 840                 845

Asp Glu Lys Asn Pro Leu Tyr Lys Tyr Tyr Glu Glu Thr Gly Asn Tyr
                        850                 855                 860

Leu Thr Lys Tyr Ser Lys Lys Asp Asn Gly Pro Val Ile Lys Lys Ile
            865                 870                 875                 880

Lys Tyr Tyr Gly Asn Lys Leu Asn Ala His Leu Asp Ile Thr Asp Asp
                            885                 890                 895

Tyr Pro Asn Ser Arg Asn Lys Val Val Lys Leu Ser Leu Lys Pro Tyr
                        900                 905                 910

Arg Phe Asp Val Tyr Leu Asp Asn Gly Val Tyr Lys Phe Val Thr Val
                        915                 920                 925

Lys Asn Leu Asp Val Ile Lys Lys Glu Asn Tyr Glu Val Asn Ser
            930                 935                 940

Lys Cys Tyr Glu Glu Ala Lys Lys Leu Lys Lys Ile Ser Asn Gln Ala
            945                 950                 955                 960

Glu Phe Ile Ala Ser Phe Tyr Asn Asn Asp Leu Ile Lys Ile Asn Gly
                            965                 970                 975

Glu Leu Tyr Arg Val Ile Gly Val Asn Asn Asp Leu Leu Asn Arg Ile
                        980                 985                 990

Glu Val Asn Met Ile Asp Ile Thr  Tyr Arg Glu Tyr Leu  Glu Asn Met
                        995                 1000                1005

Asn Asp Lys Arg Pro Pro Arg  Ile Ile Lys Thr Ile  Ala Ser Lys
                        1010                1015                1020

Thr Gln Ser Ile Lys Lys Tyr  Ser Thr Asp Ile Leu  Gly Asn Leu
                        1025                1030                1035

Tyr Glu  Val Lys Ser Lys Lys  His Pro Gln Ile Ile  Lys Lys Gly
                        1040                1045                1050
```

<210> SEQ ID NO 2
<211> LENGTH: 594
<212> TYPE: PRT
<213> ORGANISM: Artificial Sequence
<220> FEATURE:
<223> OTHER INFORMATION: Super piggyBac

<400> SEQUENCE: 2

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Val Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Ser Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Val Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365
```

```
Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
                420                 425                 430

Pro Gln Met Val Met Tyr Tyr Asn Gln Thr Lys Gly Gly Val Asp Thr
                435                 440                 445

Leu Asp Gln Met Cys Ser Val Met Thr Cys Ser Arg Lys Thr Asn Arg
        450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
                500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Lys Glu Val Pro Gly Thr Ser
530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
                580                 585                 590

Cys Phe

<210> SEQ ID NO 3
<211> LENGTH: 340
<212> TYPE: PRT
<213> ORGANISM: Artificial Sequence
<220> FEATURE:
<223> OTHER INFORMATION: Sleeping Beauty

<400> SEQUENCE: 3

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
                20                  25                  30

Lys Val Pro Arg Ser Ser Val Gln Thr Ile Val Arg Lys Tyr Lys His
                35                  40                  45

His Gly Thr Thr Gln Pro Ser Tyr Arg Ser Gly Arg Arg Arg Tyr Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly Arg Ser Ala Arg Lys Lys Pro Leu Leu Gln Asn Arg His Lys
        115                 120                 125
```

```
Lys Ala Arg Leu Arg Phe Ala Thr Ala His Gly Asp Lys Asp Arg Thr
130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
            165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
            245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
            325                 330                 335

Ala Thr Lys Tyr
            340

<210> SEQ ID NO 4
<211> LENGTH: 340
<212> TYPE: PRT
<213> ORGANISM: Artificial Sequence
<220> FEATURE:
<223> OTHER INFORMATION: Sleeping Beauty 100X (SB100X)

<400> SEQUENCE: 4

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Tyr Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
130                 135                 140
```

```
Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
                260                 265                 270

Pro Asp Leu Asn Pro Ile Glu Asn Leu Trp Ala Glu Leu Lys Lys Arg
            275                 280                 285

Val Arg Ala Arg Arg Pro Thr Asn Leu Thr Gln Leu His Gln Leu Cys
        290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340
```